United States Patent
Park et al.

(10) Patent No.: US 12,228,518 B2
(45) Date of Patent: Feb. 18, 2025

(54) EARLY DIAGNOSIS AND MANAGEMENT OF NITROGEN DEFICIENCY IN PLANTS UTILIZING RAMAN SPECTROSCOPY

(71) Applicants: TEMASEK LIFE SCIENCES LABORATORY LIMITED, Singapore (SG); MASSACHUSETTS INSTITUTE OF TECHNOLOGY, Cambridge, MA (US)

(72) Inventors: Bong Soo Park, Singapore (SG); Rajeev J. Ram, Cambridge, MA (US); Chung Hao Huang, Singapore (SG); Gajendra Pratap Singh, Singapore (SG); Nam-Hai Chua, Singapore (SG)

(73) Assignees: TEMASEK LIFE SCIENCES LABORATORY LIMITED, Singapore (SG); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 138 days.

(21) Appl. No.: 17/999,312

(22) PCT Filed: May 20, 2021

(86) PCT No.: PCT/SG2021/050276
§ 371 (c)(1),
(2) Date: Nov. 18, 2022

(87) PCT Pub. No.: WO2021/236015
PCT Pub. Date: Nov. 25, 2021

(65) Prior Publication Data
US 2023/0184684 A1    Jun. 15, 2023

(30) Foreign Application Priority Data

May 21, 2020   (SG) .......................... 10202004759U

(51) Int. Cl.
*G01N 21/65* (2006.01)
*A01C 21/00* (2006.01)
(Continued)

(52) U.S. Cl.
CPC .......... *G01N 21/65* (2013.01); *A01C 21/007* (2013.01); *G01N 21/84* (2013.01); *G01N 33/0098* (2013.01); *G01N 2021/8466* (2013.01)

(58) Field of Classification Search
CPC .... G01N 21/65; G01N 21/84; G01N 33/0098; G01N 2021/8466; A01C 21/007; A01C 21/00
See application file for complete search history.

(56) References Cited

U.S. PATENT DOCUMENTS

2005/0282229 A1* 12/2005 Su ...................... G01N 33/6818
                                                            435/7.1
2016/0335477 A1* 11/2016 Young .................... G01N 21/59

FOREIGN PATENT DOCUMENTS

| CN | 108007916 A | * 5/2018 | ............. G01N 21/65 |
| WO | 00/78217 A1 | 12/2000 | |
| WO | 02/077608 A2 | 10/2002 | |

OTHER PUBLICATIONS

Butler et al Butler, H. J. et al. (2019). Observation of nutrient uptake at the adaxial surface of leaves of tomato (*Solanum lycopersicum*) using Raman spectroscopy. Analytical Letters, 53(4), 536â562 (Year: 2019).*

(Continued)

*Primary Examiner* — Dominic J Bologna
*Assistant Examiner* — Carlos Perez-Guzman
(74) *Attorney, Agent, or Firm* — Rothwell, Figg, Ernst and Manbeck, P.C.

(57) ABSTRACT

The present invention relates to the use of a Raman spectral signature of nitrate, as a biomarker for an early, real-time
(Continued)

diagnosis of nitrogen status in growing plants in a non-invasive or non-destructive way in order to detect nitrogen deficiency before the onset of any visible symptoms. The early, real-time diagnosis of nitrogen deficiency in plants makes it possible to correct nitrogen deficiency for the avoidance of negative effects on the yield and biomass of growing plants or leafy vegetables.

20 Claims, 19 Drawing Sheets

Specification includes a Sequence Listing.

(51) Int. Cl.
  G01N 21/84 (2006.01)
  G01N 33/00 (2006.01)

(56) References Cited

OTHER PUBLICATIONS

CN_108007916_A_I Translation (Year: 2018).*
Butler, H.J. et al., "Observation of nutrient uptake at the adaxial surface of leaves of tomato (*Solanum lycopersicum*) using Raman spectroscopy", Analytical Letters, Sep. 4, 2019, vol. 53, No. 4, pp. 536-562.
Butler, H.J. et al., "Application of vibrational spectroscopy techniques to non-destructively monitor plant health and development", Analytical Methods, Apr. 2, 2015, vol. 7, No. 10, pp. 4059-4070.
Huang, C. H. et al., "Early Diagnosis and Management of Nitrogen Deficiency in Plants Utilizing Raman Spectroscopy", Frontiers in Plant Science, Jun. 5, 2020, vol. 11, Article 663, pp. 1-13.
Gupta, S. et al., "Portable Raman leaf-clip sensor for rapid detection of plant stress", Scientific reports, Nov. 19, 2020, vol. 10, No. 20206, pp. 1-10.
Lew, T.T.S. et al., "Species-independent analytical tools for next-generation agriculture", Nature Plants, Nov. 30, 2020, vol. 6, pp. 1408-1417.
International Search Report issued in PCT/SG2021/050276 dated Jul. 30, 2021, 4 pgs.
Notice of Allowance dated Aug. 21, 2024 issued in corresponding U.S. Appl. No. 17/999,331. (8 pages).
Vanessa E. de Oliveira et al., "Carotenes and carotenoids in natural biological samples: a Raman spectroscopic analysis", Journal of Raman Spectroscopy, 2010, 41, pp. 642-650. (9 pages).
Keara A. Franklin et al., "The Roles of Phytochromes in Adult Plants", E. Schafer and F. Nagy (eds.), Photomorphogenesis in Plants and Bacteria, 2006, 3rd ed., pp. 475-497. (24 pages).
Cai, X. et al., "Effects of shading on leaf morphology, photosynthetic characteristics, and growth of Ilex asprella", Journal of Tropical and Subtropical Botany, Feb. 29, 2020, vol. 28, No. 1, pp. 25-34.
Zou, C.M. et al., "Response of photosynthesis and growth to weak light regime in four legume species", Chin J of Plan Ecology, Dec. 31, 2015, vol. 39, No. 9, pp. 909-916.
Sebastiani, F. et al., "Dissecting Adaptation Mechanisms to Contrasting Solar Irradiance in the Mediterranean Shrub *Cistus incanus*", Int J Mol Sci, Jul. 23, 2019, vol. 20, No. 14, Article 3599 (pp. 1-20).
Fan, Y. et al., "Effect of shading and light recovery on the growth, leaf structure, and photosynthetic performance of soybean in a maize-soybean relay-strip intercropping system", PLoS One, May 31, 2018, vol. 13, No. 5, Article e0198159 (pp. 1-15).
Panigrahy, M. et al., "Shade tolerance in *Swarnaprabha* rice is associated with higher rate of panicle emergence and positively regulated by genes of ethylene and cytokinin pathway", Sci Rep, May 2, 2019, vol. 9, No. 1, Article 6817 (pp. 1-17).
Schulz, H. et al., "Potential of NIR-FT—Raman spectroscopy in natural carotenoid analysis", Biopolymers, Mar. 31, 2005, vol. 77, No. 4, pp. 212-221.
Sng, B.J.R. et al., "Rapid metabolite response in leaf blade and petiole as a marker for shade avoidance syndrome", Plant Methods, Oct. 27, 2020, vol. 16, Article 144 (pp. 1-17).
International Search Report issued in PCT/SG2021/050275 dated Jul. 14, 2021, 3 pages.

* cited by examiner

A

B

A

B

A
Pak Choi (Time course)

B
Choy Sum (Time course)

C
Pak Choi (Recovery)

D
Choy Sum (Recovery)

EARLY DIAGNOSIS AND MANAGEMENT OF NITROGEN DEFICIENCY IN PLANTS UTILIZING RAMAN SPECTROSCOPY

CROSS-REFERENCE TO RELATED APPLICATIONS

This application is a 35 U.S.C. 371 National Phase Entry Application from PCT/SG2021/050276 filed May 20, 2021, which claims priority to and the benefit of Singapore patent application Ser. No. 10202004759U, filed on May 21, 2020, the disclosures of which are incorporated herein by reference in their entirety.

The instant application contains a Sequence Listing which has been submitted via EFS-Web and is hereby incorporated by reference in its entirety. Said Sequence Listing, created on Nov. 18, 2022, is named 2577-260US2.txt and is 4096 bytes in size.

BACKGROUND OF THE INVENTION

The present invention relates to the use of Raman spectroscopy to identify a spectral biomarker that is associated with nitrogen deficiency, which then can be used for the early, real-time diagnosis of nitrogen deficiency and ultimately for remediation of nitrogen deficiency.

The publications and other materials used herein to illuminate the background of the invention or provide additional details respecting the practice, are incorporated by reference, and for convenience are respectively grouped in the Bibliography.

Precision farming deploys intelligent systems to increase agricultural productivity and profitability while protecting the environment. Sensors can play a valuable role in providing timely, spatially-resolved measurements of biophysical parameters that can guide management decisions. For example, fertilizer application can be tailored to specific crop conditions. Nitrogen is generally the most important and also the major limiting factor for crop growth and agriculture productivity (Kant et al., 2011; Masclaux-Daubresse et al., 2010). Nitrogen concentration in green vegetation is related to chlorophyll content and photosynthesis potential. Nitrogen-limiting conditions promote leaf senescence lowering yield and biomass in plants (Kant et al., 2011). However, when nitrogen supply surpasses vegetation's nutritional needs, the excess is eliminated by runoff and infiltration into the water table leading to pollution of aquatic ecosystems resulting in eutrophication. Further environmental pollution is linked to the production of nitrous oxides and the fossil fuels consumed in the production of ammonia (Ju et al., 2009; Santamaria, 2006). Precision agriculture seeks to limit this pollution by using sensor data to deliver precisely enough fertilizer to meet the plants nutritional needs.

Previous work on optical sensing of nitrogen deficiency has relied on measuring the effect of nutrient stress on chlorophyll content and foliage reflectance and transmittance, via a reduction in chlorophyll, which were found to be affected by nitrogen deficiency. However, changes in the spectral reflectance due to nitrogen deficiency have been shown to overlap with the spectral response due to other nutrient deficient stresses (Emmett W. Chappelle et al., 1992; J. Peñuelas et al., 1994; Tracy M. Blackmer et al., 1996) and to general stress response (Altangerel et al., 2017; Carter, 1994; Charles Farber and Kurouski, 2018; Lee Sanchez et al., 2019).

Raman spectroscopy, discovered in 1928 by C. V. Raman and K. S. Krishnan (Raman and Krishnan, 1928), measures the inelastic scattering of laser light that results in a characteristic 'fingerprint' of vibrational frequencies for various molecular species present in a sample. Early experiments on aqueous salts of nitrate established the strong Raman peaks near 1049 cm$^{-1}$ associated with the symmetric stretching of the three oxygen atoms of the nitrate ion (Grassmann, 1932; Silveira and Bauer, 1932).

Raman spectroscopy has been used to analyse nitrogen-deficiency in microalgae (Huang et al., 2010; Philip Heraud et al., 2006) and several well-identified Raman peaks corresponding to triglycerides, carotenoids or chlorophylls were reported. However, changes in the intensity of these peaks are also seen in plants experiencing biotic and abiotic stresses (Altangerel et al., 2017; Baranski et al., 2005; Pudney et al., 2011). Near-infrared hyperspectral imaging has been used to diagnose nitrogen deficiency in cucumber plants based on chlorophyll distribution map of the plant (Shi Ji-Yonga, 2012). However, this method can only be used at the late stage of nitrogen deficiency when chlorophyll degradation occurs; besides, it is not specific to nitrogen stress because chlorophyll degradation can be induced by many biotic and abiotic stresses. U.S. Pat. No. 7,215,420 discloses the use of Raman spectroscopy to measure nitrogen content of agriculture products such as fruits and leaves as a measure of quality.

Precision agriculture seeks to limit this pollution by using sensor data to deliver precisely enough fertilizer to meet the plants nutritional needs. This necessitates a method that can precisely sense and timely alert on the nitrogen levels in an urban farming setting such that remedial steps may be taken before appearance of any morphological symptoms in plants. It is desired to develop methods and systems that can be used to non-destructively and non-invasively measure changes of nitrate in vivo and to assess nitrogen status, such as nitrogen deficiency, of plants.

SUMMARY OF THE INVENTION

The present invention relates to the use of Raman spectroscopy to identify a spectral biomarker that is associated with nitrogen status, such as nitrogen deficiency, which then can be used for the early, real-time diagnosis of nitrogen status, such as nitrogen deficiency, and ultimately for remediation of nitrogen deficiency. More specifically, the present invention relates to the use of a Raman spectral signature of nitrate, as a biomarker for an early, real-time diagnosis of nitrogen status in growing plants in a non-invasive or non-destructive way in order to detect nitrogen deficiency before the onset of any visible symptoms. The early, real-time diagnosis of nitrogen deficiency in plants makes it possible to correct nitrogen deficiency for the avoidance of negative effects on the yield and biomass of growing plants or leafy vegetables.

The invention uses Raman spectral signature of nitrate as a biomarker for an early, real-time diagnosis of nitrogen deficiency in growing plants in a non-invasive or non-destructive way, wherein plants need not be "destroyed" in order to detect the adverse effect of nitrogen deficiency upon their health, and ultimately the yield. Raman spectroscopy at near-infrared (830 nm) excitation wavelength accurately detects changes in the concentration of nitrate due to nitrogen deficiency by changes in intensity of a Raman signal at 1046 cm$^{-1}$. Changes in nitrate concentrations are detected before and while morphological changes occurred, highlighting nitrate as an indicator of nitrogen deficiency and Raman spectroscopy as a predictive tool for early diagnosis. Raman spectroscopy-based signatures can be used in a hand-held Raman spectroscope to detect nitrogen deficiency. Any Raman spectroscope can be used in the invention for detecting nitrogen deficiency.

The early, real-time diagnosis of nitrogen deficiency provides a window period within which the adverse effects of nitrogen deficiency can be reversed without negatively affecting the yield of growing plants, or leafy vegetables. Plants affected by nitrogen deficiency tend to undergo leaf senescence thereby reducing the yield and biomass in plants. Early diagnosis of nitrogen deficiency enables treating the nitrogen deficiency in time to remedy, and to ensure yield in plants, including leafy vegetables growing in, particularly, artificial urban farming settings.

Thus, in one aspect, the present invention provides a method of diagnosing nitrogen deficiency in a plant. In accordance with this aspect, the method comprises:
(a) obtaining a Raman spectra of nitrate in vivo and in situ (i.e., in planta) in tissue of a plant leaf at a first point in time, wherein the Raman spectra includes a peak characteristic of nitrate;
(b) obtaining a Raman spectra of nitrate in vivo and in situ in the tissue of the plant leaf at a second point in time, wherein the Raman spectra includes the peak characteristic of nitrate;
(c) comparing intensity of the peak characteristic of nitrate from the Raman spectra obtained at the first point of time with intensity of the peak characteristic of nitrate from the Raman spectra obtained at the second point of time; and
(d) determining if there is a decrease in the intensity of the peak characteristic of nitrate from the Raman spectra obtained at the second point in time,
wherein a relative decrease in intensity of the peak characteristic of nitrate from the Raman spectra obtained at the second point of time is indicative of nitrogen deficiency.

In some embodiments, the tissue of the plant leaf is a leaf blade. In some embodiments, the peak characteristic of nitrate in the Raman spectra is 1046 cm$^{-1}$. In other embodiments, the Raman spectra is obtained using near-infrared excitation wavelength. In some embodiments, the near-infrared excitation wavelength is 830 nm. In other embodiments, obtaining the Raman spectra is non-invasive and non-destructive to the tissue of the plant leaf.

In another aspect, the present invention provides a method of reversing the development of nitrogen deficiency in a plant comprising: (a) diagnosing nitrogen deficiency in a plant according to a method described herein and (b) adding fertilizer to the plants.

BRIEF DESCRIPTION OF THE FIGURES

(FIG. 2A). Classification of nitrate sufficient and deficient samples based on the first two principal components (PCs) is shown. (FIG. 2B). The principal component 2 (PC2) clearly shows the presence of 1046 cm$^{-1}$ Raman peak which we have identified as nitrate Raman peak in plant leaves.

(FIG. 3A). Classification of nitrate sufficient and deficient samples based on the first two principal components (PCs) is shown. (FIG. 3B). The principal component 2 (PC2) clearly shows the presence of 1046 cm$^{-1}$ Raman peak which we have identified as nitrate Raman peak in plant leaves.

(FIG. 4A), Morphological phenotype, scale bar, 1 cm. (FIG. 4B), Total chlorophyll content of leaf No. 4 was analysed in +N and −N plants. n=8 (biologically independent experiments). Data are mean values, n=8 (biologically independent experiments) and individual data points are shown as overlays. FW; fresh weight. P values are given in Table 2. (FIG. 4C), Nitrate content of leaf No. 4 was analysed in +N or −N plants. Data are mean values, n=12 (biologically independent experiments) and individual data points are shown as overlays. Asterisks indicate statistically significant difference compared with +N. *P<0.05, P<0.01, *P<0.001; two-tailed t-test. FW; fresh weight. Supplementary Table 2 shows P values. (FIG. 4D), ORE1 transcript levels were analysed by qRT-PCR in leaf No. 4 samples of +N or −N plants. Data are mean values, n=10 (biologically independent experiments) and individual data points are shown as overlays. Asterisks indicate statistically significant difference compared with +N. *P<0.05, P<0.01, *P<0.001; two-tailed t-test. Tables 1 and 2 show primer sets and P values, respectively. (FIG. 4E). Schematic of the Raman spectroscopy setup. (FIG. 4F). Three-week-old seedlings of WT transferred into +N and −N hydroponic medium and grown for 3 days. Leaf No. 4 was used for measurement of Raman spectra. Peak intensities are mean values, n=12 (biologically independent experiments). (FIG. 4G). Raman spectra of 100 mM Ca(NO$_3$)$_2$, KNO$_3$ and NH$_4$NO$_3$. Identification of the nitrate peak by standard pure chemicals. a.u; arbitrary unit.

(FIG. 5A) and (FIG. 5B). Three-week-old seedlings of WT transferred into phosphate-sufficient (+P), phosphate-deficient (−P), potassium-sufficient (+K), or potassium-deficient (−K) hydroponic medium and grown for 3 days. Leaf No 4 was used for measurement of Raman spectra. Peak intensities are mean values, n=12 (biologically independent experiments). (FIG. 5C). Comparison of peak intensity of the 1046 cm$^{-1}$ peak in +N, −N, +P, —P, +K or −K plants. Region of Raman spectra between 1010 and 1100 cm$^{-1}$ is shown from FIG. 1e, FIGS. 2a and 2b. a.u; arbitrary unit. (FIG. 5D). The intensity of the 1046 cm$^{-1}$ peak was analysed. Data are mean values, n=12 (biologically independent experiments) and individual data points are shown as overlays. Asterisks indicate statistically significant difference compared with +N, +P or +K, respectively. *P<0.05, P<0.01, *P<0.001; two-tailed t-test. P values are shown in Table 3.

(FIG. 6A), PCR of the knock-out line of nrt2.1-2 was conducted by left/right genomic primer (LP and RP) and the left T-DNA border primer (LBb1.3). n=3 (biologically independent experiments). (FIG. 6B), Expression levels of NRT2.1 and NRT2.2 were analysed by qRT-PCR in WT and mutant plants. Data are mean values ±S.D., n=5 (biologically independent experiments).

(FIG. 7A), Morphological phenotype, scale bar, 1 cm. n=8 (biologically independent experiments). (FIG. 7B), Total chlorophyll content of leaf No. 4 samples was analysed in +N and −N plants. Data are mean values, n=8 (biologically independent experiments) and individual data points are shown as overlays. FW; fresh weight. P values are shown in Table 4. (FIG. 7C), Nitrate content of leaf No. 4 samples was analysed in +N and −N plants. Data are mean values, n=8 (biologically independent experiments) and individual data points are shown as overlays. Asterisks indicate statistically significant difference compared with +N. *P<0.05, P<0.01, *P<0.001; two-tailed t-test. FW; fresh weight. Supplementary Table 4 shows P values. (FIG. 7D), ORE1 transcript levels were analysed by qRT-PCR in leaf No. 4 samples of +N and −N plants Data are mean values, n=8 (biologically independent experiments) and individual data points are shown as overlays. Asterisks indicate statistically significant difference compared with +N. *P<0.05, P<0.01, *P<0.001; two-tailed t-test. Tables 1 and 4 show primer sets and P values, respectively. (FIG. 7E) and (FIG. 7F), Leaf No. 4 samples of +N or −N plants were measured by Raman spectroscopy. The 1046 $cm^{-1}$ region of Raman spectrum shows the nitrate peak of WT or nrt2.1-2 in +N or −N condition. Data are mean values, n=12 (biologically independent experiments) and individual data points are shown as overlays. Asterisks indicate statistically significant difference compared with Col-0 (+N). *P<0.05, P<0.01, *P<0.001; two-tailed t-test. P values are shown in Table 5. a.u; arbitrary unit.

(FIG. 9A), Morphological phenotype, scale bar, 1 cm. n=8 (biologically independent experiments). (FIG. 9B), Total chlorophyll content of leaf No. 4 samples was analysed in +N and −N plants. Data are mean values, n=8 (biologically independent experiments) and individual data points are shown as overlays. Asterisks indicate statistically significant difference compared with +N. *P<0.05, P<0.01, *P<0.001; two-tailed t-test. FW; fresh weight. P values are shown in Table 2. (FIG. 9C), Nitrate content of leaf No. 4 samples was analysed in +N and −N plants. Data are mean values, n=12 (biologically independent experiments) and individual data points are shown as overlays. Asterisks indicate statistically significant difference compared with +N. *P<0.05, P<0.01, *P<0.001; two-tailed t-test. FW; fresh weight. P values are shown in Supplementary Table 2. (FIG. 9D), ORE1 orthologous gene transcript levels were analysed by qRT-PCR in leaf No. 4 samples of Pak Choi and Choy Sum grown under +N or −N condition for 5 days. Data are mean values, n=12 (biologically independent experiments) and individual data points are shown as overlays. Asterisks indicate statistically significant difference compared with +N. *P<0.05, P<0.01, *P<0.001; two-tailed t-test. Tables 1 and 2 show primer sets and P values, respectively. (FIG. 9E) and (FIG. 9F), Leaf No. 4 samples from +N and −N plants were measured by Raman spectroscopy. Only the 1046 $cm^{-1}$ of Raman shift ($cm^{-1}$) is shown. Data are mean values, n=12 (biologically independent experiments) and individual data points are shown as overlays. Asterisks indicate statistically significant difference compared with +N. *P<0.05, P<0.01, *P<0.001; two-tailed t-test. P values are shown in Table 5. a.u; arbitrary unit.

(FIG. 10A). Pak Choi; (FIG. 10B). Choy Sum. See FIG. 9e legend for details.

(FIG. 11A), Three-week-old seedlings of WT (Col-0) were transferred into +N or −N hydroponic medium. Leaf No. 4 samples were measured by Raman spectroscopy at various time points after transfer to −N medium. n=10 (biologically independent experiments). ((FIG. 11B), *Arabidopsis* plants grown under −N for 3 days were transferred into +N medium. Plants samples (R) at 0 day were same with samples grown for 3 days under −N medium. Samples were taken at various time points for 4 days. R; plants in the recovery +N medium, Scale bar, 0.5 cm ((FIG. 11A) and ((FIG. 11B). a.u; arbitrary unit. n=10 (biologically independent experiments). (C), Nitrate content of leaf No. 4 was analysed in +N or recovery plants (R). Data are mean values, n=12 (biologically independent experiments) and individual data points are shown as overlays. Asterisks indicate statistically significant difference compared with +N. *P<0.05, P<0.01, *P<0.001; two-tailed t-test. FW; fresh weight. Table 2 shows P values. ((FIG. 11D), ORE1 transcript levels were analysed by qRT-PCR in samples (leaf #4) of +N or recovery plants (R). Data are mean values, n=5 (biologically independent experiments) and individual data points are shown as overlays. Asterisks indicate statistically significant difference compared with +N. *P<0.05, P<0.01, *P<0.001; two-tailed t-test. Tables 1 and 6 show primer set and P values, respectively.

(FIG. 14A) and (FIG. 14B), Three-week old seedlings of two-week old seedlings of Pak Choi (*Brassica rapa chinensis*) and Choy Sum (*Brassica rapa* var. parachinensis) were transferred into +N or −N hydroponic medium. Leaf No. 4 samples were measured by Raman spectroscopy at various time points after transfer to −N medium. n=10 (biologically independent experiments). (FIG. 14C) and (FIG. 14D), Pak Choi and Choy Sum plants grown under −N for 3 days were transferred into +N medium. Plants samples (R) at 0 day were same with samples grown for 3 days under −N medium. Samples were taken at various time points for 3 days. n=5 (biologically independent experiments). R; recovery plant, Scale bar, 0.5 cm. a.u; arbitrary unit.

(FIG. 19A) and (FIG. 19B), Nitrate content of leaf No. 4 was analysed in +N or recovery plants (R) in Pak Choi (FIG. 19A) and Choy Sum (FIG. 19B). Data are mean values, n=5 (biologically independent experiments) and individual data points are shown as overlays. Asterisks indicate statistically significant difference compared with +N. *$P<0.05$, $P<0.01$, *$P<0.001$; two-tailed t-test. FW; fresh weight. (FIG. 19C) and (FIG. 19D), ORE1 orthologous gene transcript levels were analysed by qRT-PCR in leaf No. 4 samples of +N or recovery plants (R) in Pak Choi (FIG. 19C) and Choy Sum (FIG. 19D). Data are mean values, n=5 (biologically independent experiments) and individual data points are shown as overlays. Asterisks indicate statistically significant difference compared with +N. *$P<0.05$, $P<0.01$, *$P<0.001$; two-tailed t-test. Tables 1 and 7 show primer sets and P values, respectively

DETAILED DESCRIPTION OF THE INVENTION

Figure 1:
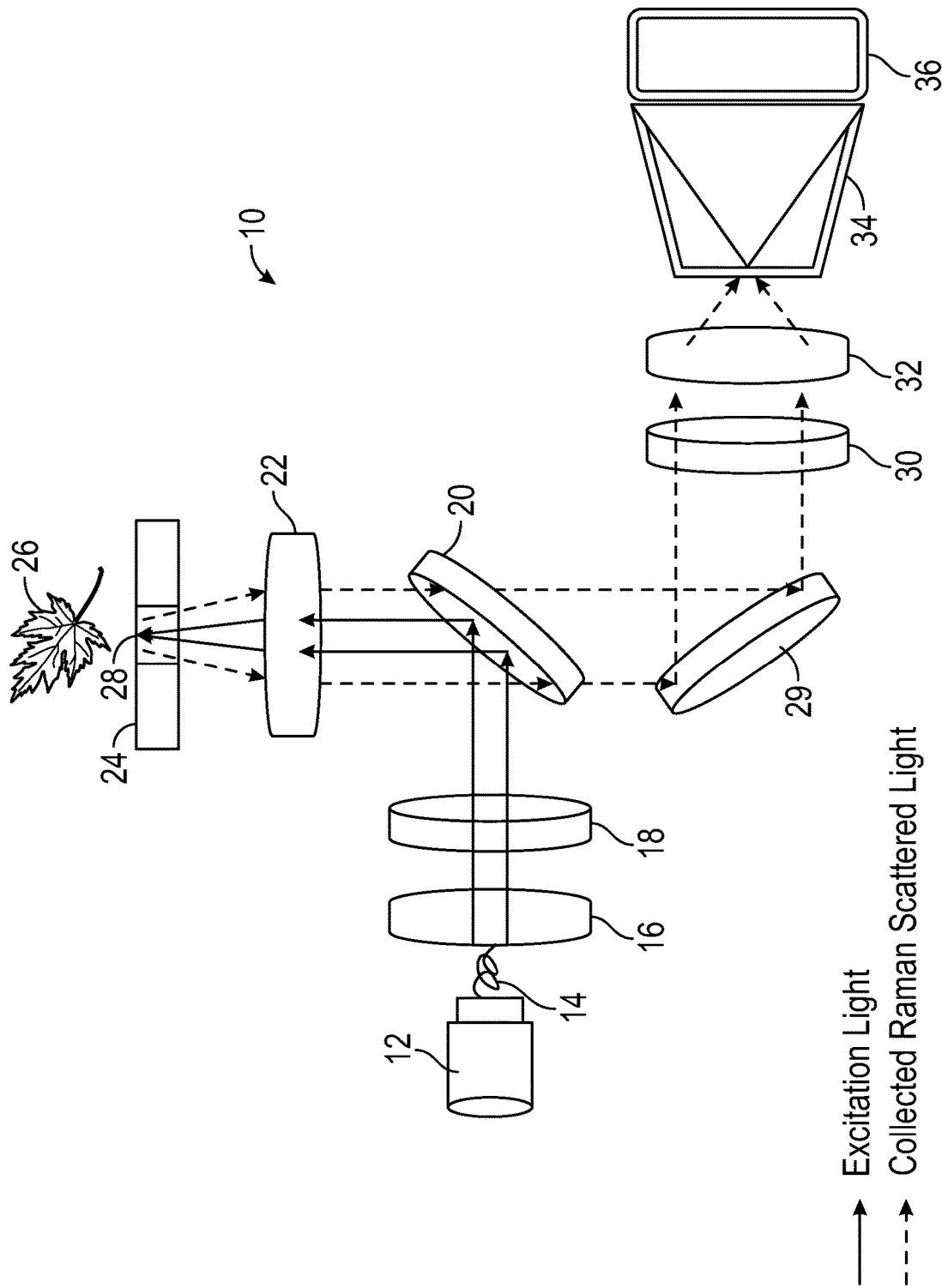
FIG. 1 is a schematic representation of an exemplary system for collecting Raman spectra data.

The present invention relates to the use of Raman spectroscopy to identify a spectral biomarker that is associated with nitrogen status, such as nitrogen deficiency, which then can be used for the early, real-time diagnosis of nitrogen status, such as nitrogen deficiency, and ultimately for remediation of nitrogen deficiency. More specifically, the present invention relates to the use of a Raman spectroscopy signature of nitrate, as a biomarker for an early, real-time diagnosis of nitrogen status in growing plants in a non-invasive or non-destructive way in order to detect nitrogen deficiency before the onset of any visible symptoms. The early, real-time diagnosis of nitrogen deficiency in plants makes it possible to correct nitrogen deficiency for the avoidance of negative effects on the yield and biomass of growing plants or leafy vegetables.

Thus, in one aspect, the present invention provides a method of diagnosing nitrogen deficiency in a plant. In accordance with this aspect, the method comprises:
(a) obtaining a Raman spectra of nitrate in vivo and in situ (i.e., in planta) in tissue of a plant leaf at a first point in time, wherein the Raman spectra includes a peak characteristic of nitrate;
(b) obtaining a Raman spectra of nitrate in vivo and in situ in the tissue of the plant leaf at a second point in time, wherein the Raman spectra includes the peak characteristic of nitrate;
(c) comparing intensity of the peak characteristic of nitrate from the Raman spectra obtained at the first point of time with intensity of the peak characteristic of nitrate from the Raman spectra obtained at the second point of time; and
(d) determining if there is a relative decrease in the intensity of the peak characteristic of nitrate from the Raman spectra obtained at the second point in time,
wherein a relative decrease in intensity of the peak characteristic of nitrate from the Raman spectra obtained at the second point of time is indicative of nitrogen deficiency.

In some embodiments, the tissue of the plant leaf is a leaf blade. In some embodiments, the peak characteristic of nitrate in the Raman spectra is 1046 $cm^{-1}$. In other embodiments, the Raman spectra is obtained using near-infrared excitation wavelength. In some embodiments, the near-infrared excitation wavelength is 830 nm. In other embodiments, obtaining the Raman spectra is non-invasive and non-destructive to the tissue of the plant leaf.

In another aspect, the present invention provides a method of reversing the development of nitrogen deficiency in a plant comprising: (a) diagnosing nitrogen deficiency in a plant according to a method described herein and (b) adding fertilizer to the plants.

In laser Raman spectroscopy, monochromatic laser light is directed onto a particular material to be tested. A sensitive detection system then detects light returning, or scattered, from the material. The majority of the light returning from the material is scattered elastically at the same wavelength of the original projected laser light. A very small fraction of the light returning from the material is scattered inelastically at a wavelength different from that of the original projected laser light in a manner known as Raman scattering. Raman scattered light is then separated from Rayleigh scattered light with the use of filters, optical gratings, prisms, and other wavelength selection techniques. The energy difference between scattered Raman light and the incident laser light, conventionally represented in wave numbers ($cm^{-1}$), is related to the vibrational, rotational, or liberational states, or combinations thereof, of various molecules in the material being evaluated. Each of the peaks in the resulting Raman spectrum corresponds to a particular Raman active vibration of a molecule or a component thereof. The Raman energy shift is independent of the wavelength of the directed laser light. That is, the energy difference corresponding to the elastically and inelastically scattered light for a particular material remains constant for that material. The characteristic results from Raman scattering can be used to locate, identify and quantify concentrations of a material. The absolute intensities of the resulting Raman peaks are directly related to the concentration of the Raman-active molecules in the material.

The present invention relates to the use of Raman spectroscopy to identify a biomarker that is associated with nitrogen deficiency in plants, which then can be used for the early, real-time diagnosis of nitrogen deficiency in plants and ultimately for remediation of nitrogen deficiency in plants. More specifically, the present invention relates to the use of a Raman spectral signature of nitrate as a biomarker for an early, real-time diagnosis of nitrogen deficiency in growing plants in a non-invasive or non-destructive way in order to detect the adverse effect of the nitrogen deficiency on plant health, and ultimately plant yield. The early, real-time diagnosis of nitrogen deficiency provides a window period within which the adverse effects of the nitrogen deficiency can be reversed or remediated without negatively affecting the yield of growing plants, including leafy vegetables.

The early, real-time diagnosis of the nitrogen deficiency provides a window period within which the adverse effects of the nitrogen deficiency can be reversed without negatively affecting the yield of growing plants, or leafy vegetables. Leaves of plants affected by nitrogen deficiency tend to undergo senescence thereby reducing yield in plants, including leafy vegetables. Early diagnosis of nitrogen deficiency enables treating the deficiency in time to remedy, and to ensure yield of plants, including leafy vegetables particularly growing in artificial urban farming settings.

As shown herein, the concentration of nitrate in leaf tissue is a biomarker for nitrogen deficiency and can be used to monitor the development and progression of nitrogen deficiency, as well as the remediation of nitrogen deficiency. Nitrate has been found to exhibit characteristic Raman scattering, the results of which show up in a distinct spectral position, signal strength, and spectral width. More specifically, and as shown herein using the described Raman spectroscopy system, nitrate exhibits strong characteristic Raman scattering signal at 1046 $cm^{-1}$. The intensity of the Raman signal is directly related to the concentration of nitrate. Thus, a decrease in the relative intensity of the Raman signal is indicative of a decrease in the concentration of nitrate, and an increase in the relative intensity of the Raman signal is indicative of an increase in the concentration of nitrate. As shown herein, a relative decrease in the concentration of nitrate is indicative of nitrogen deficiency.

In some embodiments, Raman spectra are collected using a purpose-built Raman spectroscopy system shown in FIG. 1 and described in detail in Example 1. In one embodiment, a Raman spectroscopy system used herein is designed for 830 nm excitation. In general, the sample holder featured a 100 μm thick fused silica sampling window used for both excitation and collection of the Raman signal. An aspheric lens is used to focus the excitation light and collect the Raman scattered light. The lens is chosen with a depth of focus >1 mm so that Raman signal from the entire cross-section of a leaf is collected. The excitation laser used with this system is a fiber coupled laser (Innovative Photonic Solutions, USA) operating at 830 nm delivering approximately 100 mW of laser power to the sample. Light is delivered from the laser to collimating optics via a 105 micron core multimode fiber. The collimated light is passed through a Semrock MaxLine Laser Line 830 filter (Semrock Inc., USA) to remove any amplified spontaneous emission from the laser and any background generated within the delivery fiber. The filtered light is coupled into the optical path of the excitation lens by a Semrock long pass filter (Semrock Inc., USA) operated as a dichroic mirror. Collected light is passed back through the Semrock filter and then through an additional long pass filter to further attenuate Rayleigh scattered excitation light before being delivered to the spectrometer using an F # matching lens. Spectra are acquired using Kymera 328i spectrograph (Andor, UK) employing a 600 g/mm optical grating. While an embodiment of a Raman spectroscopy has been described, it is appreciated that any Raman spectroscopy system, including different excitation laser wavelengths or different excitation and collection optical design, or different Raman signal detector such as photodiodes or CCDs, that can focus light on a plant leaf and collect Raman signature can be used for detecting nitrogen deficiency.

In practice, Raman spectra are collected for nitrate in plant material such as a plant leaf. For each sample of plant leaf, 5 spectra are collected with an integration time of 10 s per sample spot. Cosmic ray events are identified in the 10 s spectrum and removed. After cosmic ray removal, the individual 10 s spectra are smoothed across wavelength using the Savitzky-Golay filter function (MATLAB Inc., USA) with a degree of 11. A representative sample spectrum is created by taking the mean value of the five filtered and smoothed spectra at each wavelength. The sample spectrum resulting from this processing contains Raman and fluorescence signal primarily from the leaf. To generate the leaf Raman spectra presented herein any residual fluorescence is removed by performing a positive residual style polynomial subtraction as described in reference (Lieber and A., 2003). Calibration of the Raman shift is performed using a polystyrene sample with a well-known Raman spectrum (C. M. Creely et al., 2005).

In one embodiment, the concentration of nitrate is determined within plant material. In some embodiments, the plant material is leaf material. In some embodiments, the leaf material is a leaf blade. In some embodiments, Raman spectra are collected at two locations per leaf blade. In some embodiments, the locations are one on each side of the midvein of the leaf blade. Concentration levels of nitrate can be determined at different times, for example on different days, to follow any changes in the concentration of nitrate. As shown herein a decrease in the concentration of nitrate over time is indicative of nitrogen deficiency. Conversely, an increase in the concentration of nitrate subsequent to a decrease in the concentration of nitrate is indicative of remediation of nitrogen deficiency.

Raman spectroscopy is faster and easier to use than other techniques used to determine concentrations of nitrate in plant tissues, is non-invasive and not harmful to the plant, allows real-time measurements as plants grow and develop, measures the concentration of nitrate in vivo and in situ (i.e., in planta) and enables focusing on small parts of plants for the analysis of individual seedlings and specific plant tissues or cells. It can also be used to measure seed quality. These benefits of Raman spectroscopy enable the detection of the development of nitrogen deficiency by Raman spectrometry before the onset of any morphological changes in the plants. The early diagnosis of nitrogen deficiency enables the remediation of nitrogen deficiency without adverse effects on plant health and plant yield. The development of nitrogen deficiency and remediation thereof can be detected and/or followed by Raman spectrometry without destroying plant tissue. As shown herein, Raman spectroscopy can be used for early diagnosis of nitrogen deficiency and remediation of nitrogen deficiency in all growing plants, including leafy vegetables.

The early, real-time diagnosis of nitrogen deficiency provides a time window within which the development of nitrogen deficiency can be reversed or remediated before the occurrence of adverse effects on the plants including the loss of plant yield. The development of nitrogen deficiency can be reversed by any technique that increases the availability of nitrogen to plants, such as fertilization. Reducing or eliminating nitrogen deficiency is particularly beneficial for artificial urban farming settings.

In the Examples herein, it is shown that the decrease of nitrate in plants, which is indicative of nitrogen deficiency, can be detected by Raman spectroscopy as a major peak in the Raman spectra, shown herein to be the 1046 $cm^{-1}$ peak, which is a specific signature of nitrogen status in plants. Thus, Raman spectroscopy can be used to query the state of plant health, i.e., nitrogen status, in a non-invasive, non-destructive manner. Four lines of evidence support this finding.

1. We have confirmed the Raman shift at 1046 $cm^{-1}$ attributed to nitrate using standard chemicals such as calcium nitrate [$Ca(NO_3)_2$], potassium nitrate ($KNO_3$) and ammonium nitrate ($NH_4NO_3$).
2. In WT plants the 1046 $cm^{-1}$ peak intensity correlates with the nitrate content in WT *Arabidopsis* plants in starvation and recovery experiments.

3. The peak intensity is reduced in *Arabidopsis* mutant in nrt2.1/nrt2.2 which is partially blocked in nitrate uptake.
4. The peak intensity also correlates with nitrate content in two vegetables (Pak Choi and Choy Sum) in starvation and recovery condition.
5. This Raman peak is specific to nitrogen stress as its intensity is not altered in plants under −P or −K.

An important aspect of the findings herein is that nitrate deficiency can be diagnosed by its specific Raman signature as early as 3 days on the starvation medium when there is no morphological manifestation of the deficient plants. This finding facilitates plant stress management through early diagnosis of nitrogen deficiency in a non-invasive manner and allow application of appropriate remedial measures to ameliorate the stress. To this end, it is shown herein that nitrogen deficient plants can recover from nitrogen stress by returning them to a full load of nitrogen, and along with this recovery the relative nitrate peak intensity also returns to the original nitrate level. The results show that Raman spectroscopy can be deployed as a tool for precision agriculture and will be useful in the field management of crops.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Plant materials, growth conditions and preparation of plant samples: *Arabidopsis thaliana* WT (Col-0) and two vegetables, Pak Choi (*Brassica rapa chinensis*) and Choy Sum (*Brassica rapa* var. parachinensis), were used. The nrt2.1-2 mutant in the Col-0 background was obtained from the Salk Institute (Salk 035429). Seeds were germinated on 0.8% agar media containing Murashige and Skoog (MS) salts, 0.5 g/L MES and 10 g/L sucrose. *Arabidopsis* and vegetables were grown at 22° C. with 60% relative humidity in long-day conditions (16 h light/8 h dark) under white light at 100 μmol m$^{-2}$ s$^{-1}$ in a growth chamber. Plants were grown in either +N or −N medium by modified Hoagland's solution containing 2 mM CaCl$_2$ and 3 mM KCl (pH 5.8) instead of 2 mM Ca(NO$_3$)$_2$ and 3 mM KNO$_3$ (pH 5.8). For phosphate or potassium deficiency, we have replaced KH$_2$PO$_4$ with KCl, or KNO$_3$ and KH$_2$PO$_4$ with NaNO$_3$ and NaH$_2$PO$_4$, respectively. The number of biologically independent repeats in each experiment is described in figure legends.

Nrt2.1-2 mutant genotyping: *Arabidopsis* genotypes was analysed by Phire Plant Direct PCR Kit (Thermo Scientific). Briefly, 10 mg leaf sample was ground into a powder and dissolved in 10 ul dilution buffer. Total DNA extract was analysed by PCR with gene-specific primer sets shown in Table 1.

TABLE 1

Primer Sets for qRT-PCR and Genotyping Analysis

| Gene name | Primer sequence (SEQ ID NO:) |
|---|---|
| qRT-PCR | |
| ORE1 (*Arabidopsis*) | F 5'-CTTACCATGGAAGGCTAAGATGGG-3' (1)<br>R 5'-TCGGGTATTTCCGGTCTCTCAC-3' (2) |
| ORE1 (Pak Choi) | F 5'-CGATGCATCAAGAATCGGTGA-3' (3)<br>R 5'-CGGTGGCAGAGAAGAAAGTG-3' (4) |
| ORE1 (Choy Sum) | F 5'-GGGAAGTCACTTGTGGGTATG-3' (5)<br>R 5'-CTTTGTACCATCGGCACGTT-3' (6) |
| NRT2.1 (*Arabidopsis*) | F 5'-TGAGCAGGAGAAGCAGAAGA-3' (7)<br>R 5'-TTGTTGGGTGTGTTCTCAGG-3' (8) |
| NRT2.2 (*Arabidopsis*) | F 5'-GCTATGCTTTCTCGGTAGATGGTAG-3' (9)<br>R 5'-AATGTCATGTTTGGTGAGGTTAAGA-3' (10) |
| ACT2 (*Arabidopsis*) | F 5'-AGTGGTCGTACAACCGGTATTGT-3' (11)<br>R 5'-GATGGCATGAGGAAGAGAGAAAC-3' (12) |
| ACT2 (Pak Choi) | F 5'-TGCTGGATTCTGGTGATGGT-3' (13)<br>R 5'-GGCGTGTGGAAGAGAGAAAC-3' (14) |
| ACT2 (Choy Sum) | F 5'-TGCTGGATTCTGGTGATGGT-3' (15)<br>R 5'-GGCGTGTGGAAGAGAGAAAC-3' (16) |
| Genotyping | |
| LBb1.3 | 5'-ATTTTGCCGATTTCGGAAC-3' (17) |
| LP (nrt2.1-2) | 5'-GTTCTCCATGAGCTTCGTGAG-3' (18) |
| RP (nrt2.1-2) | 5'-CTTACCATGGAAGGCTAAGATGGG-3 (19)' |

Total chlorophyll content measurement: *Arabidopsis* (Col-0 and nrt2.1-2) and two vegetables (Pak Choi and Choy Sum) grown for 3 days and 5 days, respectively, on +N or −N medium were used for total chlorophyll measurement. Leaves were extracted with 80% acetone at 4° C. for 24 h in darkness. Total chlorophyll per fresh weight of leaf No. 4 samples was calculated as described previously (R. J. Porra et al., 1989). The number of biologically independent repeats in each experiment is described in figure legends.

Nitrate content measurement: Nitrate content was determined as described previously (D. A. Cataldo et al., 1975). Briefly, 100 mg leaf tissue was homogenized in 1 mL deionized water and incubated at 100° C. for 20 min. 10 μL of the supernatant was mixed with 40 ul 5% (w/v) salicylic-sulphuric acid and the mixture incubated at room temperature for 20 min. Following addition of 950 μL 8% NaOH, the mixture was placed at room temperature for 20 min before O.D. at 410 nm was measured. The number of biologically independent repeats in each experiment is described in figure legends.

RNA extraction and quantitative RT-PCR analysis: Total RNA was isolated from *Arabidopsis* (Col-0) and the two vegetables (Pak Choi and Choy Sum) using QIAGEN RNeasy Mini Kits (QIAGEN) according to the manufacturer's instructions. Reverse transcriptional reaction was performed using iScript™ cDNA Synthesis Kit (BIO-RAD) following to the manufacturer's instructions. Quantitative RT-PCR was performed using the CFS96 real-time system (BIO-RAD) with ORE1, NRT2.1, NRT2.2 specific primers and ACT2 as a reference gene, or ORE1 and ACT2 orthologous gene for two leafy vegetables (Table 1). The number of biologically independent repeats in each experiment is described in figure legends.

Raman system: FIG. 1 is a schematic representation of an exemplary system 10 for collecting Raman spectral data. In general, the system 10 is configured to generate and direct an optical excitation signal of a desired wavelength or wavelength range at a sample specimen, e.g., a leaf, collect Raman scattered light signal from the specimen, direct the collected light signal to a spectrometer to separate and measure spectral components of the collected signal, and record the spectral data.

System 10 includes an excitation laser 12. In one example, the laser operates at 830 nm delivering approximately 100 mW of laser power to the sample. In another example, the laser operates at 830 nm delivering approximately 60 mW of laser power to the sample. A suitable excitation laser is available from Innovative Photonic Solutions, USA.

In the illustrated example, the excitation light signal (solid lines) is delivered from laser 12 to collimating optics 16 (e.g., a collimating lens) via a 105-micron core multimode optical fiber 14, with high optical transmission and low attenuation for laser wavelength range The collimated light from the collimating optics 16 is passed through a bandpass filter (clean up filter) 18 to remove any amplified spontaneous emission from the laser 12 and any background generated within the fiber 14. A suitable bandpass filter includes a Semrock MaxLine Laser Line 830 filter (available from Semrock Inc., USA).

The filtered excitation light signal is coupled into an optical path of an excitation lens 22 by a dichroic mirror 20. A suitable dichroic mirror includes a Semrock long pass filter (available from Semrock Inc., USA). The optics including lens and filters are preferably made of fused silica or other low spectral background generating material in the desired Raman signal collection wavelength range.

Excitation light passing through the excitation lens 22 is directed to a sample 26 supported on a sample holder 24, and the Raman scattered signal (dashed lines) is collected by the excitation lens 22 and directed to the dichroic mirror 20. In one example, the excitation lens 22 is an aspheric lens configured to focus the excitation light signal toward the sample 26 and collect the Raman scattered light signal from the sample 26. Excitation lens 22 may have a depth of focus chosen in correspondence to the nature of the sample. In one example, where sample 26 comprises a leaf, excitation lens 22 has a depth of focus greater than 1 mm so that Raman scattered signal from the entire cross-section of the leaf is collected. Sample holder 24 may include a window 28, such as a 100 μm thick fused silica sampling window used for making the sample as flat as possible and placing it at the correct focal distance from the excitation lens. Through this window, both excitation and collection of the Raman signal is achieved.

The collected Raman scattered light signal is directed by the excitation lens 22 back through the dichroic mirror 20 onto a mirror 29. In the illustrated example, system 10 includes an additional long pass edge filter 30, which attenuates the Rayleigh scattered excitation light wavelength and through which the collected Raman scattered light signal is directed to the spectrometer.34 before being detected by the charge-coupled device (CCD) camera 36. The long pass edge filter can also be replaced by a suitable notch filter.

The filtered Raman scattered light signal is directed from filter 30 to a spectrometer 34 using an F # matching lens 32. A suitable spectrometer for acquiring spectra includes a Kymera 328i spectrograph (Andor, UK) employing a 600 g/mm optical grating. Spectral data may be recorded by a recording device 36, such as a charge-couple device ("CCD") camera thermoelectrically cooled to −80° C.

Raman spectra collection: For each sample of plant leaf, 5 Raman spectra were collected with an integration time of 10 s per sample spot. Cosmic ray events were identified in the 10 s spectra and removed. After cosmic ray removal, the individual 10 s spectra were smoothed across wavelength using the Savitzky-Golay filter function (MATLAB Inc., USA) with a degree of 11. A representative sample spectrum was created by taking the mean value of the five filtered and smoothed spectra at each wavelength. The sample spectrum resulting from this processing contained Raman and fluorescence signal primarily from the leaf. To generate the leaf Raman spectra presented in the results section any residual fluorescence was removed by performing a positive residual style polynomial subtraction as described in reference (Lieber and A., 2003). Calibration of the Raman shift was performed using a polystyrene sample with a well-known Raman spectrum (C. M. Creely et al., 2005). The number of biologically independent repeats in each experiment is described in figure legends.

Figure 2:
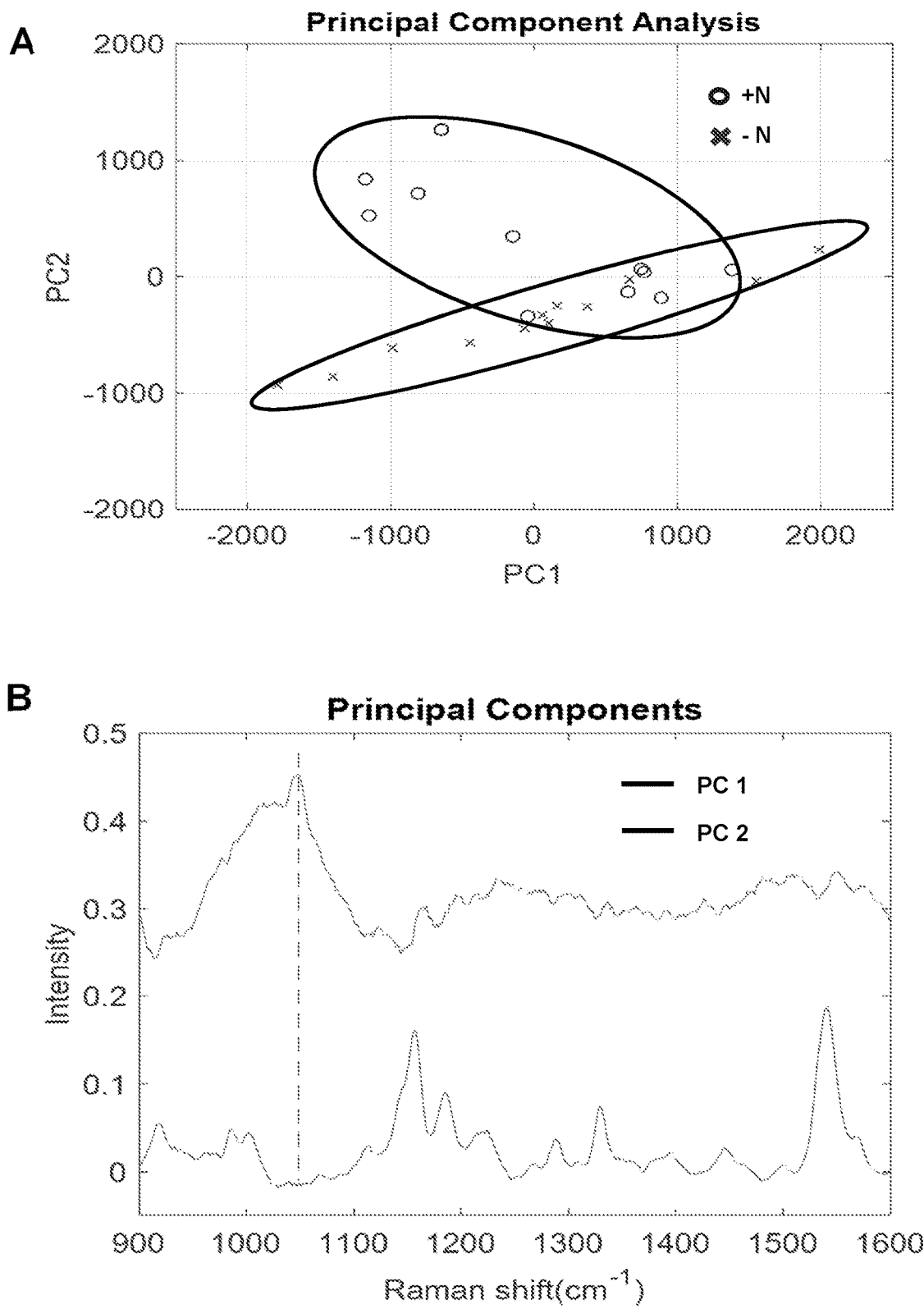
FIGS. 2A-2B show a Principal Component Analysis of Raman spectra acquired from nitrogen sufficient and nitrogen deficient *Arabidopsis* leaf samples.
Figure 3:
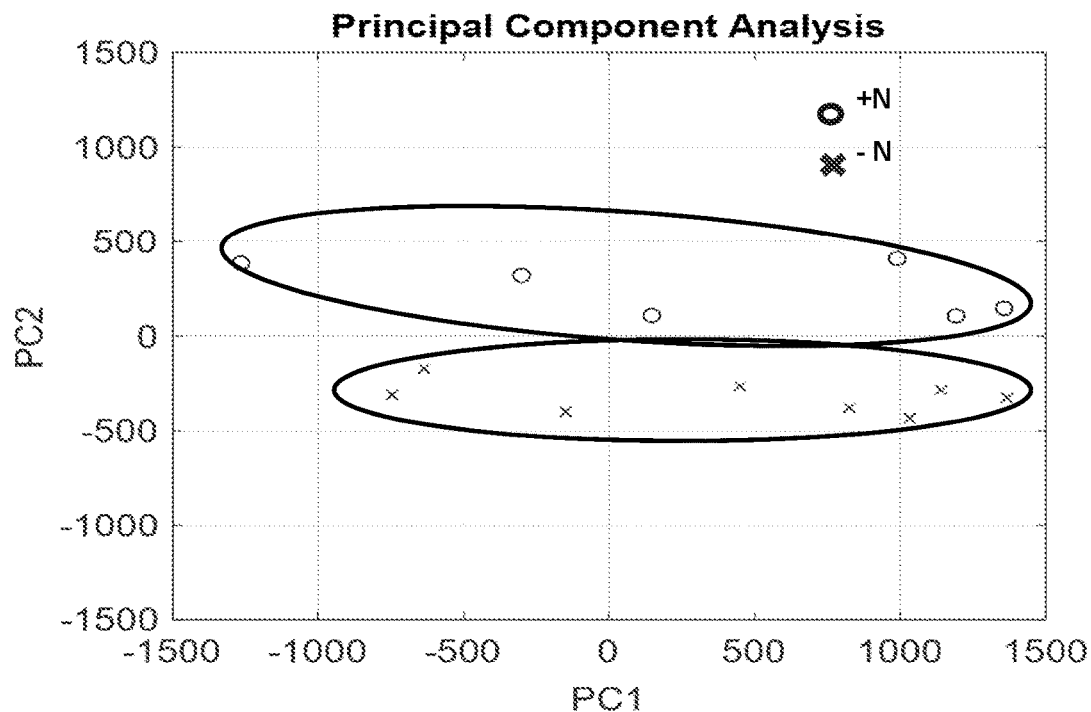
FIGS. 3A-3B show Principal Component Analysis of Raman spectra acquired from nitrogen sufficient and nitrogen deficient Pak Choi leaf samples.
Figure 3:
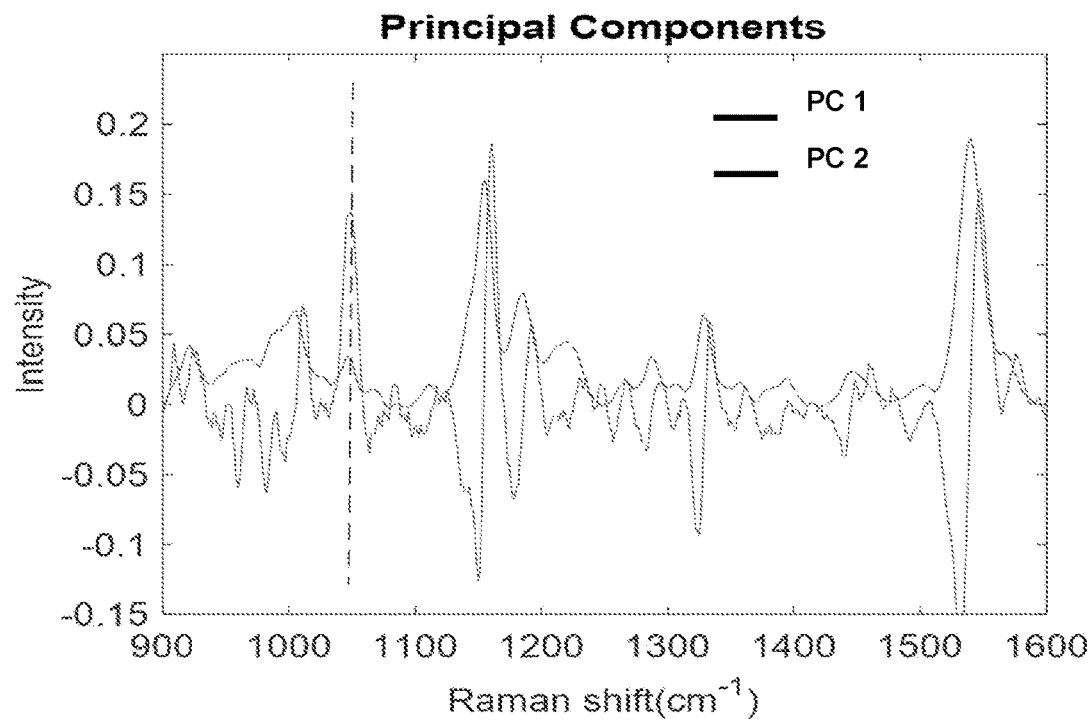

Principal component analysis (PCA): The Raman spectra were analyzed in the Raman shift wavenumber range of 900-1600 $cm^{-1}$ across 5 locations across 3 biological replicates for plants and leaves of the same age grown under +N and −N conditions. The eigenvectors of the covariance matrix of the original data set define the principal components (PCs)—the maximal directions of variance within a dataset. Taking into account the loading vectors (PC weights) of the first two principal components (PCs) (FIGS. 2A, 3A), the PCA compares +N plants with −N plants, where separation between groups was observed both for *Arabidopsis* and Pak Choy plants. PC1 corresponds to the strongest spectral lines in the data set and correspond to carotenoids. Variation in PC2 can be used to partition the Raman spectra into classes that correspond well to +N and −N conditions. The presence of peak at 1046 $cm^{-1}$—which we identify as a nitrate peak—in PC2 demonstrates that this region of Raman spectra represents one of the main differentiation factors for +N and −N plants. (FIGS. 2B, 3B).

Example 2

Relationship Between Raman Spectra and Nitrogen Status

Figure 4:
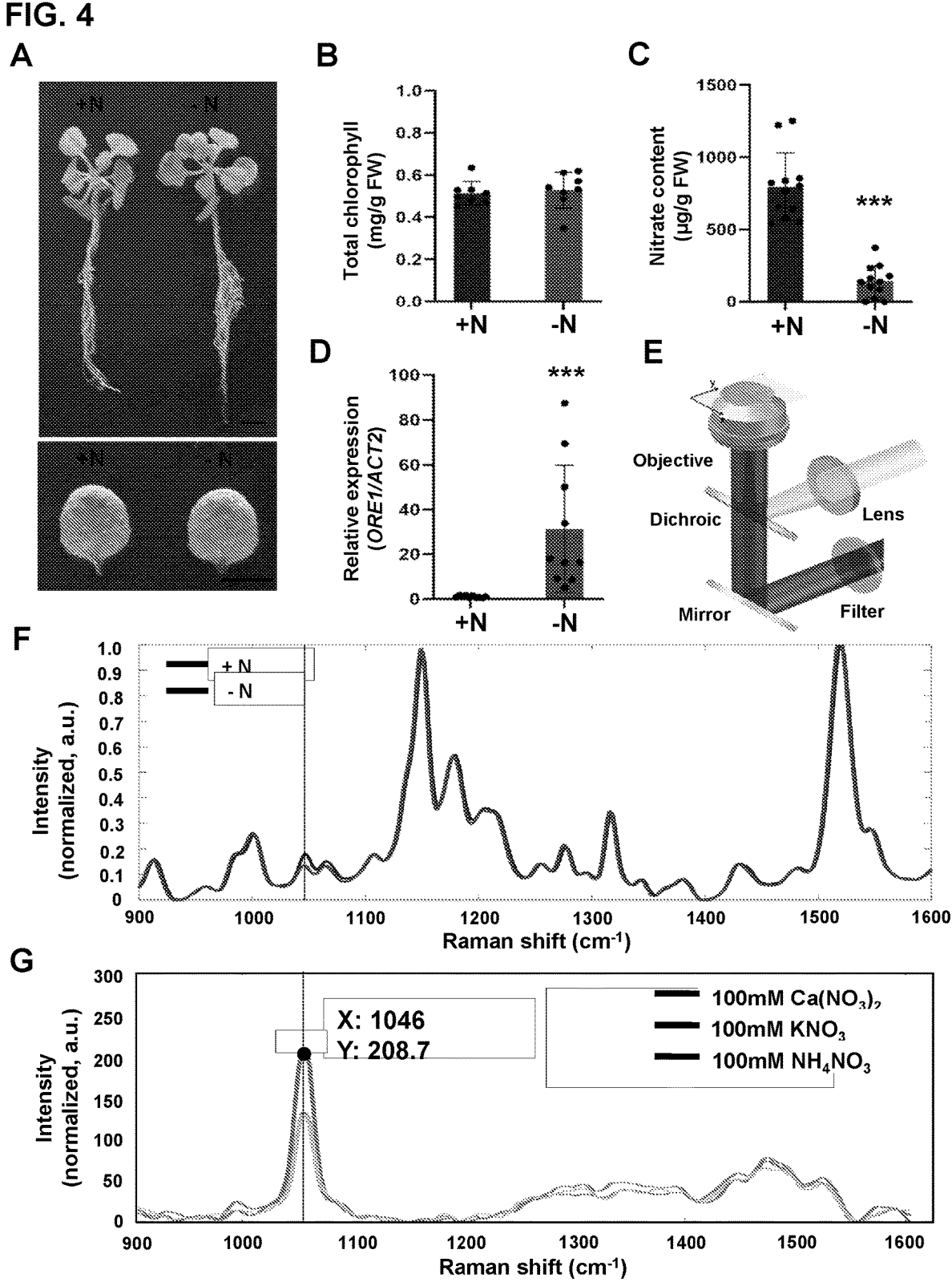
FIGS. 4A-4G show the analysis of biological/molecular phenotype and Raman spectrum of early nitrogen deficiency in *Arabidopsis*. Three-week-old seedlings of wild-type (WT) *Arabidopsis* (Col-0) were transferred into nitrogen-sufficient (+N) or nitrogen-deficient (−N) hydroponic medium and grown for an additional 3 days.

The relationship between Raman spectra and nitrogen status was investigated in the model plant *Arabidopsis thaliana* where metabolic pathways are well studied and mutants affected in specific metabolic pathways are available. Three-week-old *Arabidopsis* plants were grown under sufficient (+N; complete) or nitrogen-deficient (−N) hydroponic media. After 3 days, no visible phenotypic differences were seen between plants grown under the two conditions (FIG. 4A) and no measurable difference in the leaf chlorophyll content was detected (FIG. 4B). However, despite the similarity in visible plant phenotype and chlorophyll content, chemical analysis showed the nitrate content of −N plants was decreased by 8-fold, compared to +N plants (FIG. 4C). Moreover, plants grown under −N conditions were indeed experiencing stress responses because transcript levels of ORE1, a nitrogen-starvation induced gene (Park et al., 2018), were 30-fold higher in plants grown under −N conditions compared to +N plants (FIG. 4D). These results establish that plants mount a response to nitrogen availability within short time-periods even when visible phenotypic changes associated with nitrogen-deficient stress had not appeared.

Raman spectroscopy was explored to determine if it can be used for early diagnosis of nitrogen deficiency in plants. FIG. 4E shows a proposed Raman spectroscopy design for plant leaf analysis. The entire functioning components of Raman spectroscopy that was used in this work are shown in FIG. 1.

Raman spectra of leaves from +N and −N plants were compared and differences were found in the intensity of Raman shifts at 1000 to 1100 cm$^{-1}$ (FIG. 4F). Raman spectra of calcium nitrate [$Ca(NO_3)_2$], potassium nitrate ($KNO_3$) and ammonium nitrate ($NH_4NO_3$) was measured and all 3 compounds showed a peak at 1046 cm$^{-1}$ indicating that this Raman shift (associated with the symmetrical stretching of nitrate) is indeed the nitrate peak (FIG. 4G). These results have confirmed previous observations (D. E. Irish and Walrafen, 1967; K. Ben Mabrouk et al., 2013; Roberto Chirico et al., 2016). Note that +N plants showed a higher relative intensity of this peak whereas the −N plants a lower relative intensity.

Example 3

Confirmation of Raman Spectra Peak with Nitrate Deficiency

Figure 5:
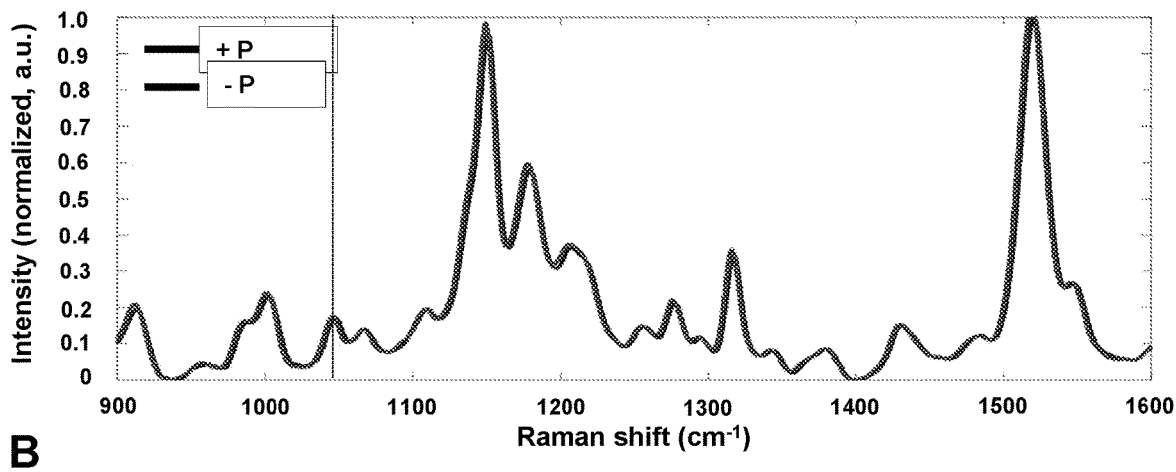
FIGS. 5A-5D show a comparison of Raman spectra under sufficient or deficient condition of 3 macronutrients (N, P and K) in *Arabidopsis*.
Figure 5:
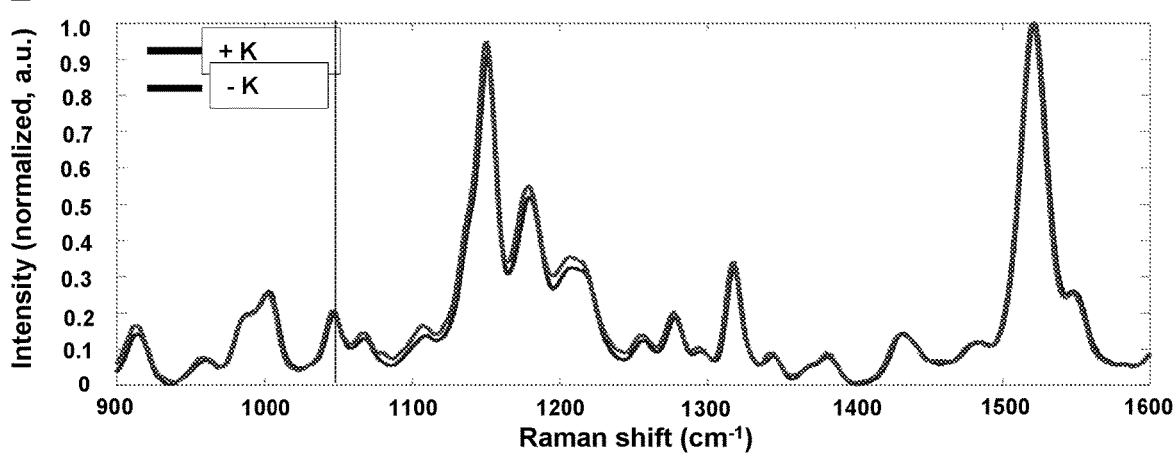
Figure 5:
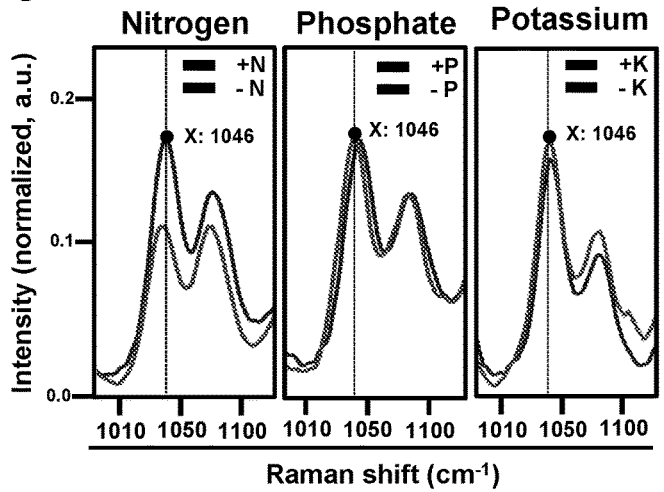
Figure 5:
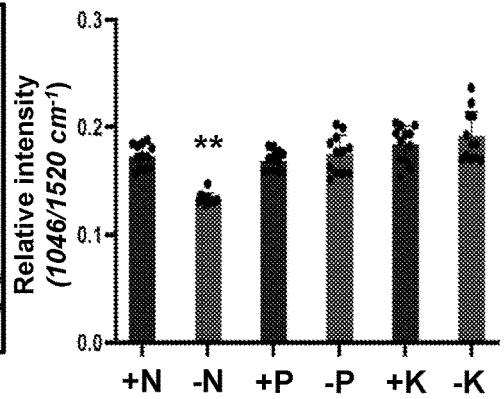

Three macronutrients are required for plant growth and development: nitrogen (N), phosphate (P) and potassium (K). To confirm the specific association of the 1046 cm$^{-1}$ peak with nitrate deficiency, Raman spectra of plants starved with P or K was determined (FIGS. 5A, 5B). Although there were changes between the Raman spectra of +P and −P plants no significant difference in the peak intensity at 1046 cm$^{-1}$ was detected. Similar results were found for +K or −K plants (FIGS. 5C, 5D). These results show that the Raman peak at 1046 cm$^{-1}$ can be used as a specific signature for plants grown under −N conditions.

Example 4

Correlation of Raman Spectra Peak with Nitrate Content

Figure 6:
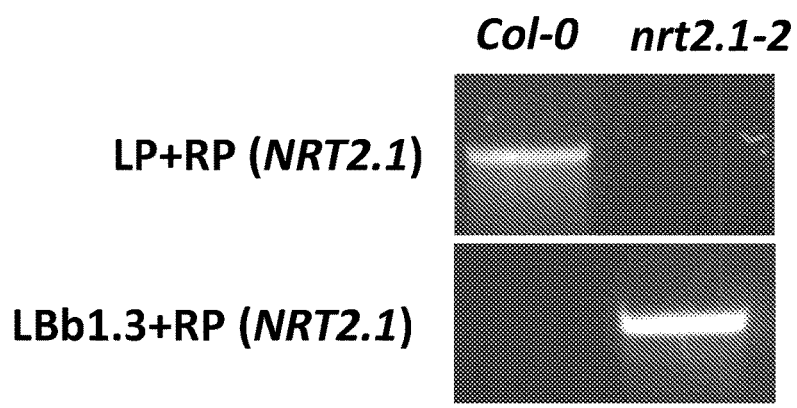
FIGS. 6A-6B show genotyping by qRT-PCR analysis of the nrt2.1-2 mutant.
Figure 6:
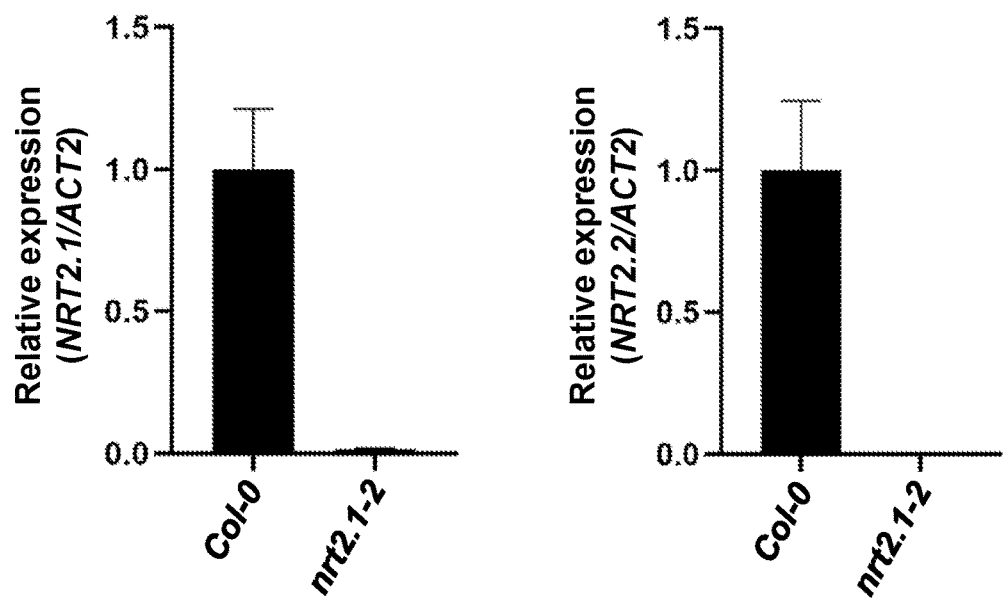
Figure 7:
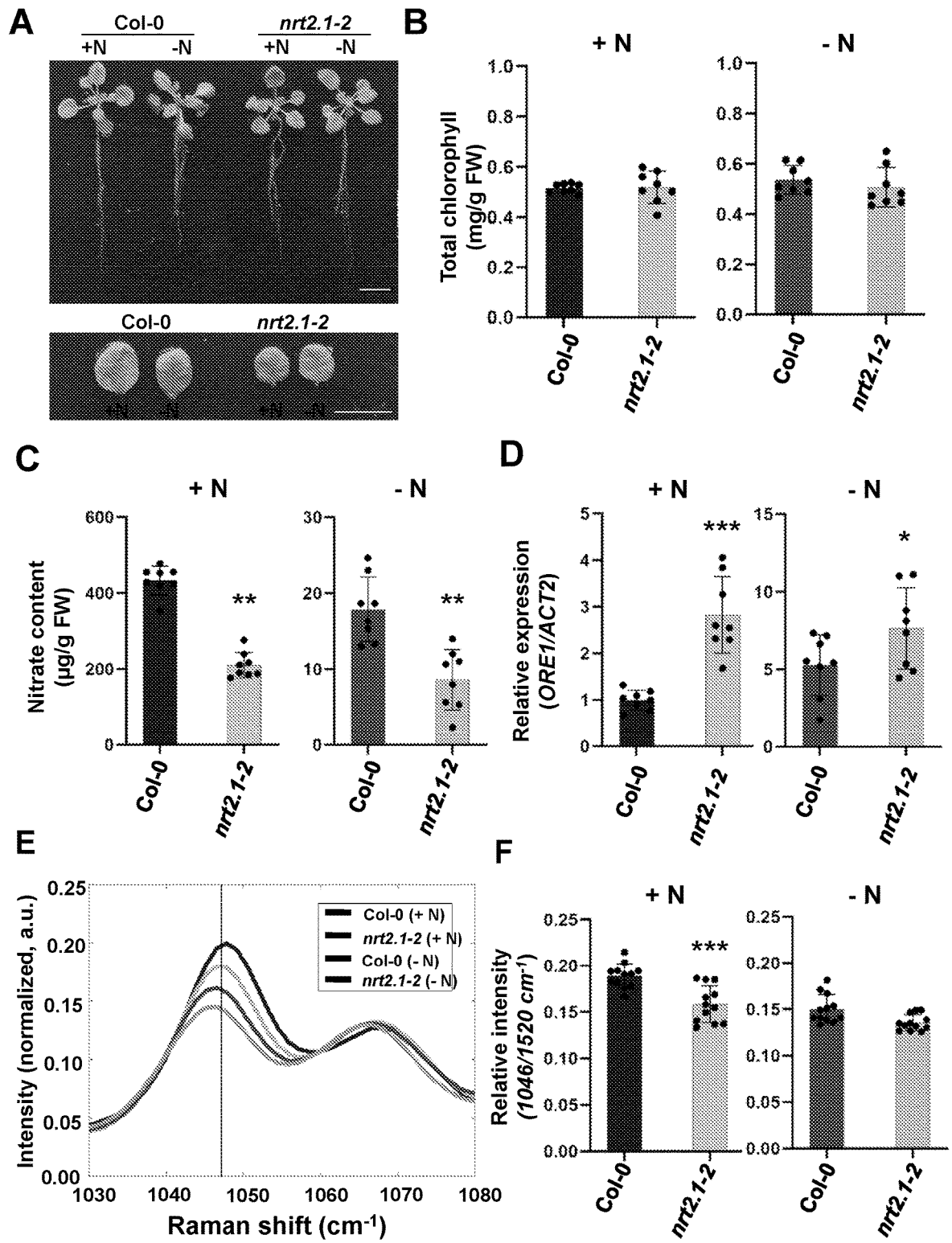
FIGS. 7A-7F show a comparative analysis of biological/molecular phenotype and Raman spectra of early nitrogen deficiency in *Arabidopsis* WT and nrt2.1-2. Three-week-old seedlings of *Arabidopsis* WT (Col-0) and nrt2.1-2 were transferred into +N or −N hydroponic medium and grown for 3 days.
Figure 8:
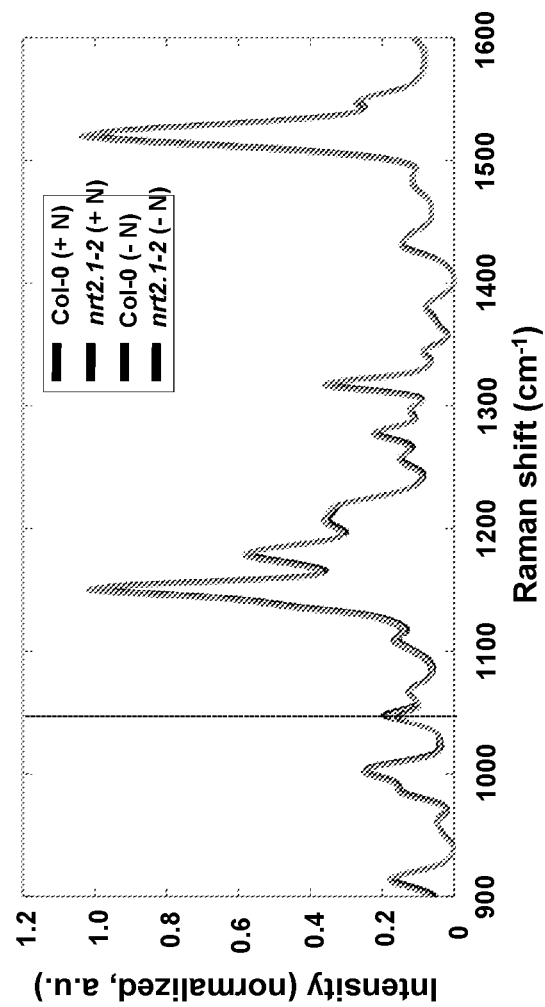
FIG. 8 shows a comparative Raman spectroscopic analysis of *Arabidopsis* WT and nrt2.1-2 under +N or −N conditions. The 900 to 1,600 ($cm^{-1}$) region of the Raman spectrum is shown. For details, see legend to FIG. 7E.

In *Arabidopsis*, several NRT2 genes are significantly expressed in roots and up-regulated by nitrogen deficiency suggesting that they may be responsible for the stimulation of the nitrate high affinity transporter system under nitrogen limiting conditions (Gansel et al., 2001; Ju et al., 2009; Okamoto et al., 2003; Orsel et al., 2002). Previously, it was shown that the influx capacity of the nrt2.1/nrt2.2 double mutants (named by nrt2.1-1 in Wassilewskija [Ws] and nrt2.1-2 in Col-0) at low nitrate concentration was decreased. The nitrate influx in nrt2.1/nrt2.2 was consistently reduced more than that in nrt2.1 at low and high nitrate concentrations (Li et al., 2007). Using nrt2.1-2 mutant, the response of nitrate deficiency was analysed. First, the genotype of the double mutant nrt2.1-2 was confirmed by checking the expression of NRT2.1 and NRT2.2 using qRT-PCR (FIG. 6). Molecular phenotypes and Raman spectra were then analysed in three-week-old wild-type (Col-0) and nrt2.1-2 mutant plants grown for 3 days under nitrogen deficient- and sufficient conditions. There was no difference in the phenotypes of WT and nrt2.1-2 plants grown under +N or −N condition (FIG. 7A) and no significant difference in leaf chlorophyll content was detected (FIG. 7B). However, chemical analysis showed that the nitrate content of nrt2.1-2 plants was 2-fold less compared to WT under both +N or −N condition (FIG. 7C). Moreover, under +N condition ORE1 transcript levels in nrt2.1-2 were slightly induced compared to +N WT plants, and under −N condition, its transcript level of nrt2.1-2 plants were 5-fold higher and 3-fold higher than WT and nrt2.1-2 under +N condition, respectively (FIG. 7D). These results show that nrt2.1-2 plants were already under moderate nitrogen deficient stress in +N condition. FIGS. 7E and 7FA show that the relative peak intensity at 1046 cm$^{-1}$ in the nrt2.1-2 mutant was significantly lower than in WT under both +N and −N conditions. These changes in 1046 cm$^{-1}$ intensity correlate with changes in nitrate content. Wider-range spectra of FIG. 7E are presented in FIG. 8.

Example 5

Extension of Raman Nitrate Peak to Crop Plants

Figure 9:
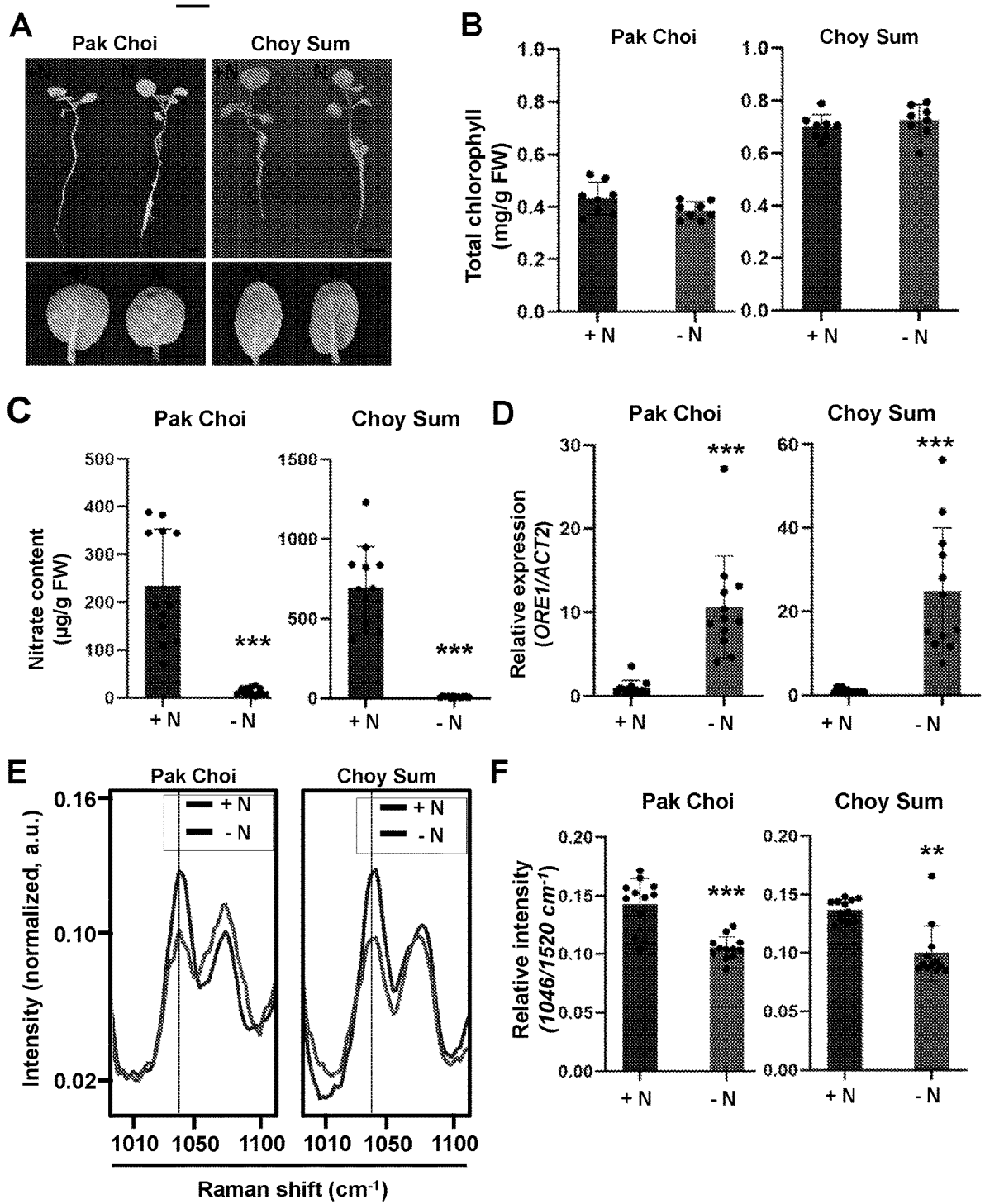
FIGS. 9A-9F show biological/molecular phenotype and Raman spectral analysis of early nitrogen deficiency in leafy vegetables, Pak Choi and Choy Sum. Two-week-old seedlings of Pak Choi (*Brassica rapa chinensis*) and Choy Sum (*Brassica rapa* var. parachinensis) were transferred into +N or −N hydroponic medium and grown for 5 days.
Figure 10:
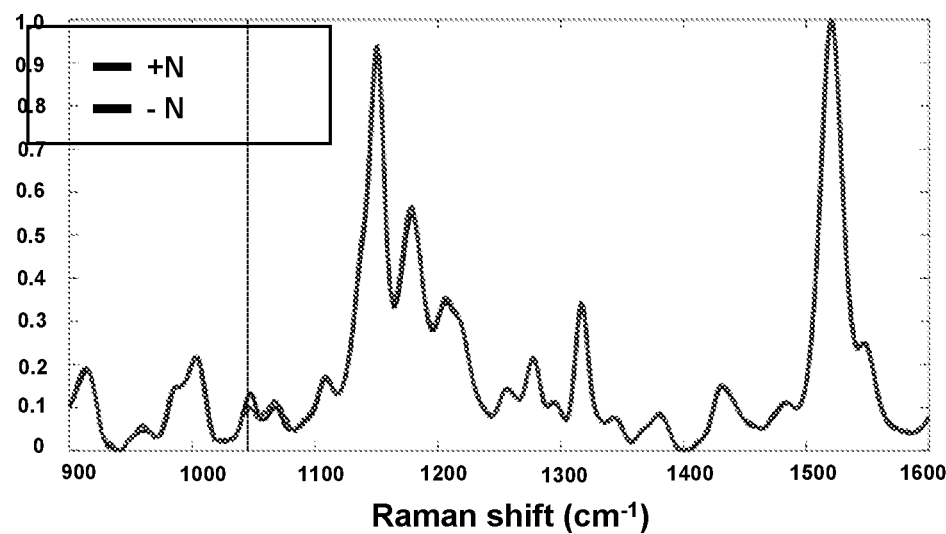
FIGS. 10A-10B show a Raman spectroscopic analysis of leafy vegetables under −N or +N condition.
Figure 10:
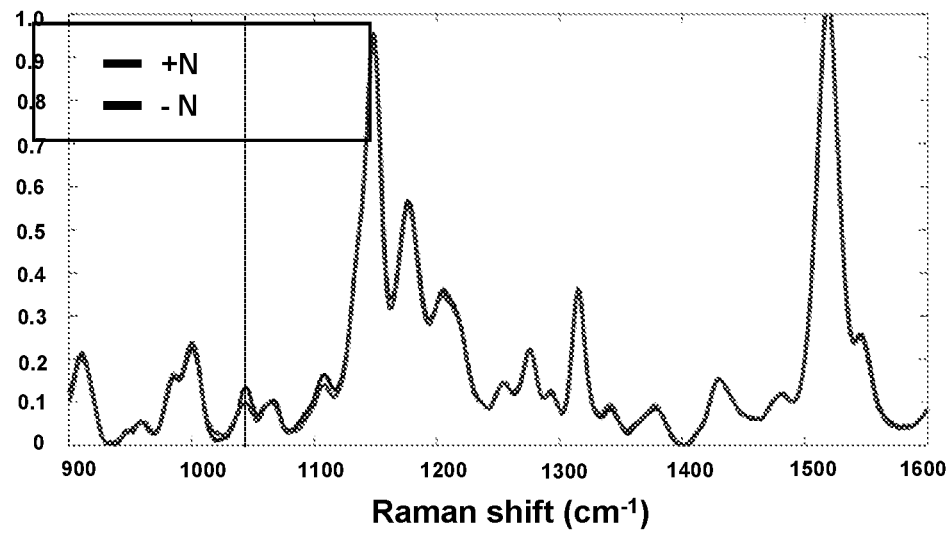

To see if the Raman nitrate peak identified using *Arabidopsis* can be extended to crop plants, Raman spectra of two leafy vegetables belonging to the Brassicaceae family: Pak Choi (*Brassica rapa chinensis*) and Choy Sum (*Brassica rapa* var. parachinensis) were analysed. As in *Arabidopsis*, two leafy vegetable plants were grown under +N or −N conditions but for 5 days. Similar to *Arabidopsis*, the two leafy vegetable plants exhibited little phenotypic differences when grown under +N or −N (FIG. 9A); neither was there a significant change in their leaf chlorophyll content (FIG. 9B). However, nitrate content was significantly decreased in −N plants (FIG. 9C). Under −N condition, ORE1 orthologous gene transcript levels in Pak Choi and Choy Sum were increased by 10-fold and 20-fold, respectively indicating the implementation of nitrogen stress responses (FIG. 9D). In both leafy vegetables, the relative intensity of the 1046 cm$^{-1}$ peak under −N condition was significantly lower than that of +N condition and the peak pattern was similar to that of WT *Arabidopsis* under −N condition (FIG. 9E, 9F). Wider-range spectra of FIG. 9E are shown in FIG. 10. Taken together, these results show that the 1046 cm$^{-1}$ nitrate peak identified by Raman spectroscopy can also be used to diagnose nitrogen status in crop plants as well.

Example 6

Management of Plant Nutritional Status

Figure 11:
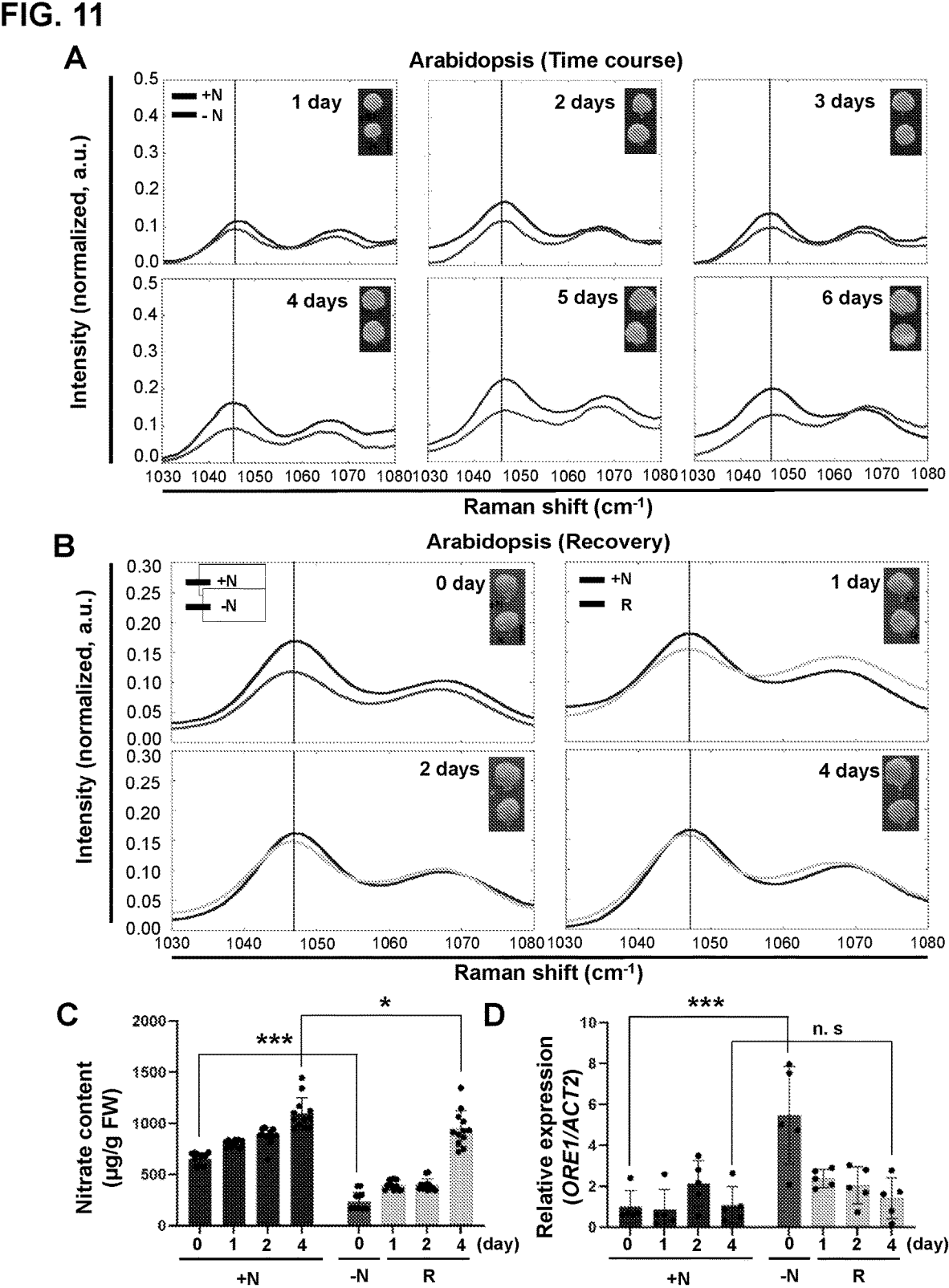
FIGS. 11A-11D show a time course analysis of *Arabidopsis* under +N, −N and recovery conditions by Raman spectroscopy.
Figure 12:
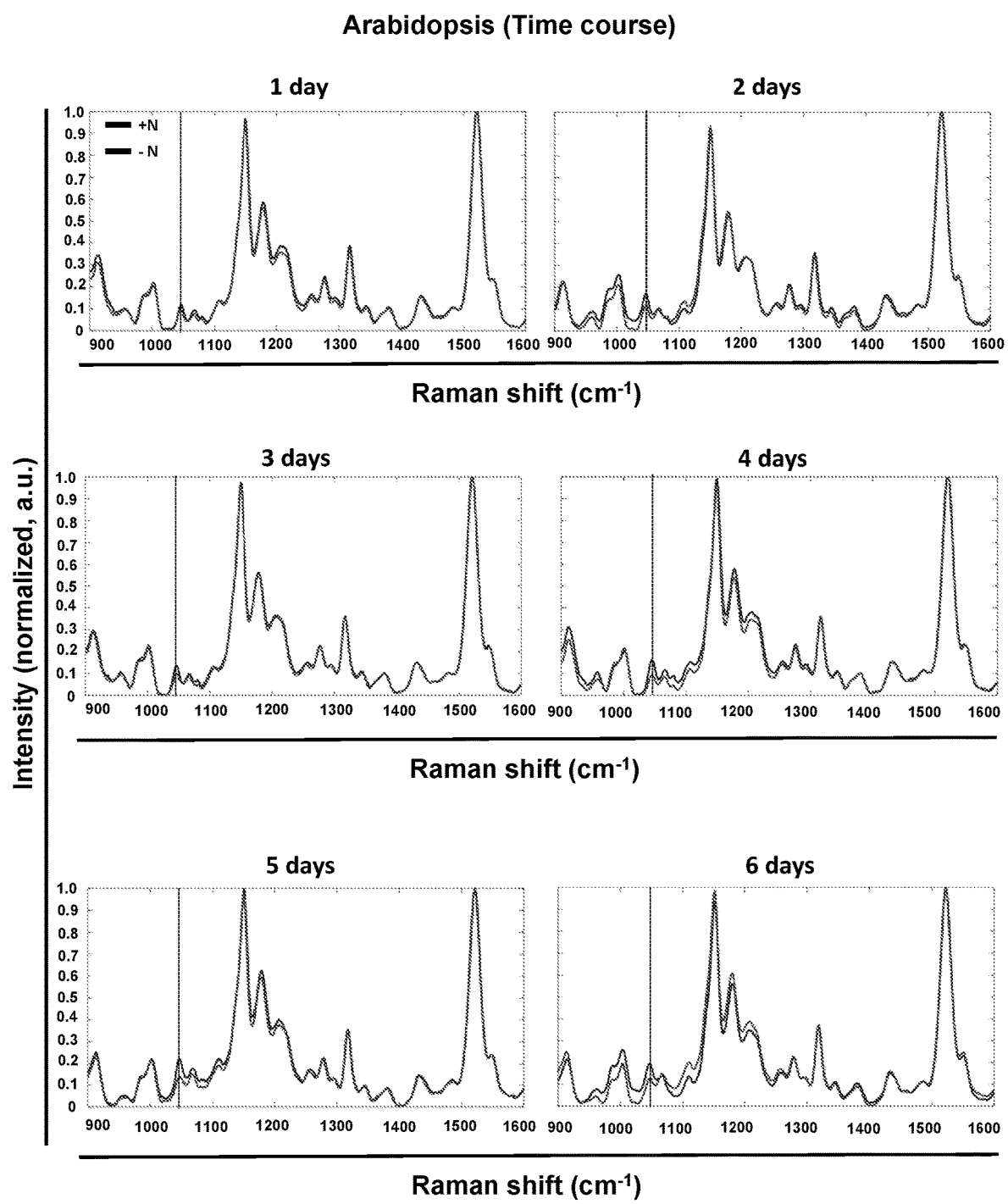
FIG. 12 shows a comparative analysis of wide-range Raman spectrum of *Arabidopsis* plants grown under +N or −N condition by time course. See FIG. 11A legend for details.
Figure 13:
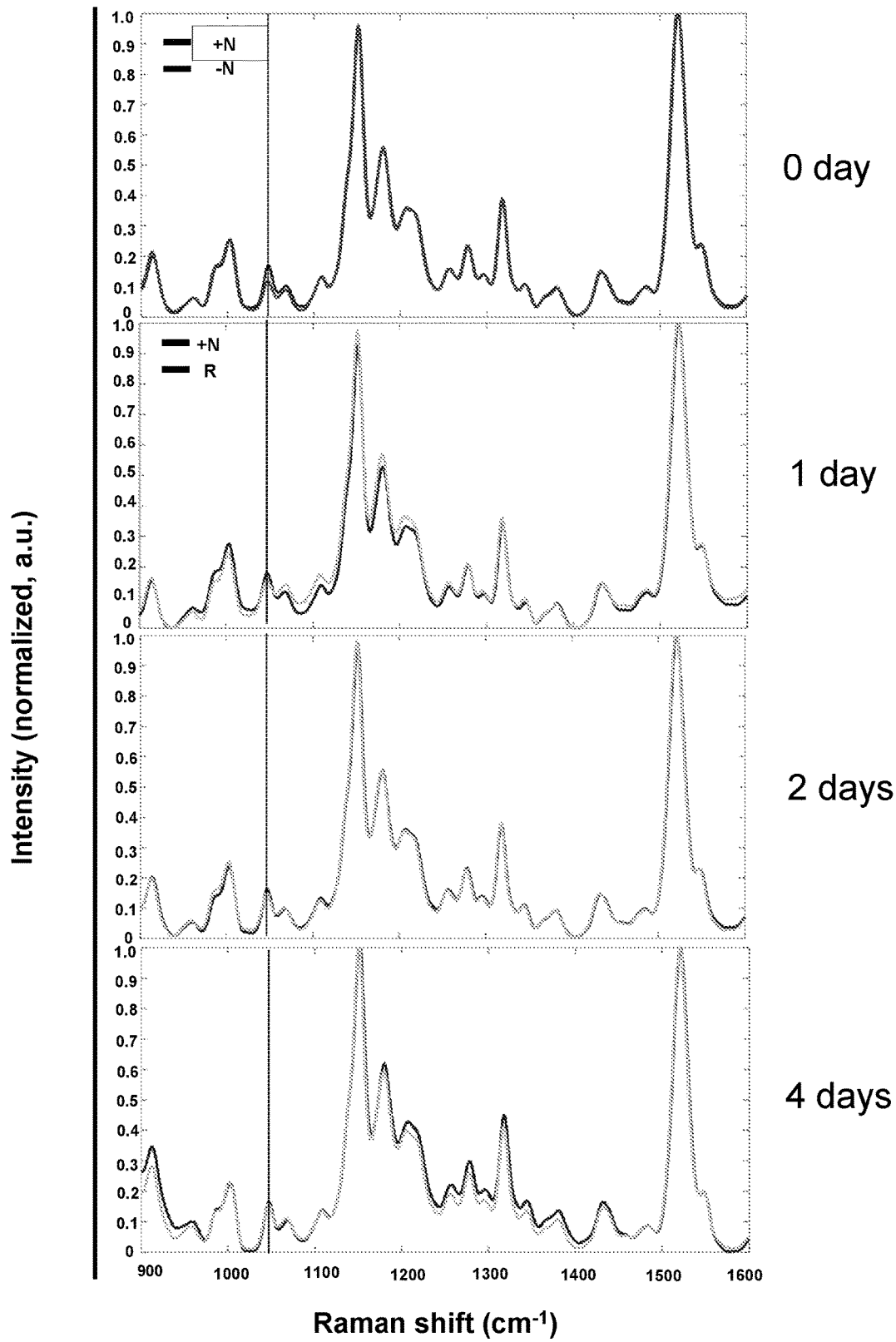
FIG. 13 shows a comparative analysis of wide-range Raman spectrum of *Arabidopsis* plants grown for recovery experiments by time course. Plants (R) were first grown in −N condition for 3 days before being returned to +N condition for an additional 3 days. See FIG. 11B legend for details.

To see if Raman spectroscopy can be integrated into the management of plant nutritional status, a time course experiments of *Arabidopsis* under −N conditions was performed. FIG. 11A shows that the 1046 cm$^{-1}$ peak intensity decreased with time upon transfer to the −N medium. To see if this decrease in peak intensity at 1046 cm$^{-1}$ can be reversed we transferred −N (day 3) plants to +N medium and followed their recovery for several days. FIG. 11B shows after one day in the +N medium nitrate peak intensity at 1046 cm$^{-1}$ was still lower than that under nitrogen sufficient condition, but the peak intensity returned to the level of that of +N plants after 4 days in the full medium. FIGS. 12 and 13 show the corresponding wider-range spectra of FIGS. 11A and 11B, respectively.

Nitrate content was measured and ORE1 transcript level was analysed of plants undergoing recovery in the full medium (FIG. 11C, 11D). Plants starved for nitrate in the −N medium for 3 days were used for the recovery experiment. Compared with +N plants, the nitrate content of these −N plants was decreased by 3-fold. However, the nitrate content returned to the +N levels after 4 days in the +N medium. Changes in the nitrate content were matched by corresponding changes in the nitrate peak intensity (FIG. 11C). Because of the nitrate replenishment, ORE1 transcript levels decreased by 3-fold after 4 days in the recovery medium (FIG. 11D).

Example 7

Management of Plant Nutritional Status in Leafy Vegetables

Figure 14:
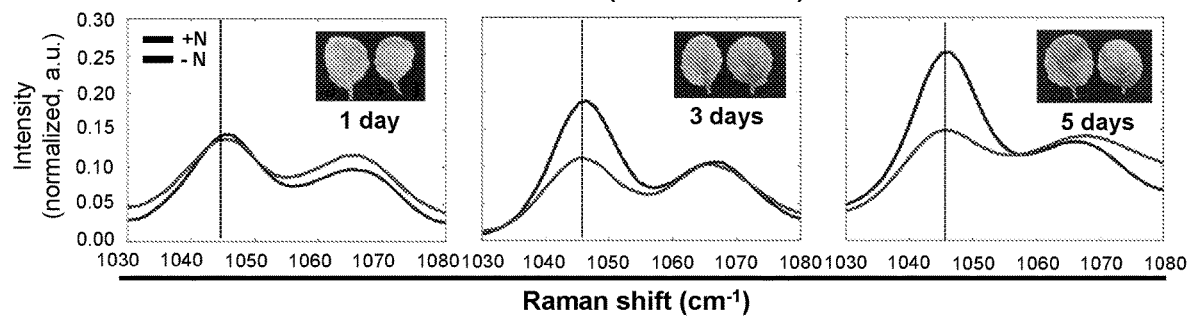
FIG. 14A-14D show a time course analysis of leafy vegetables, Pak Choi and Choy Sum under +N, −N and recovery conditions by Raman spectroscopy.
Figure 14:
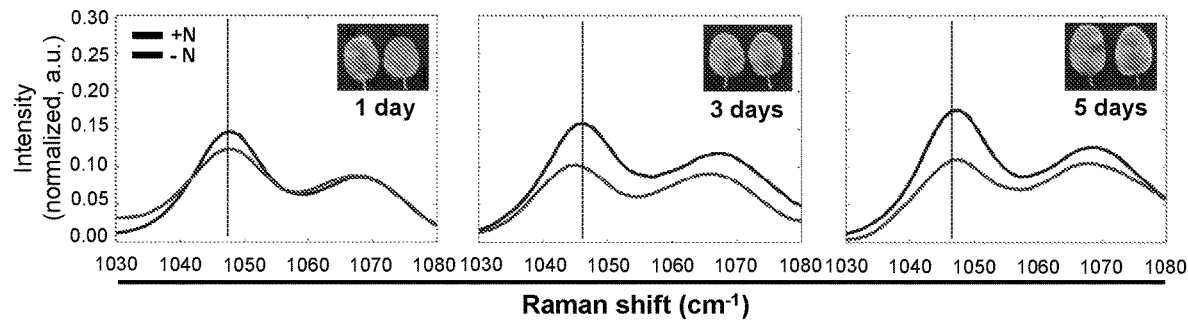
Figure 14:
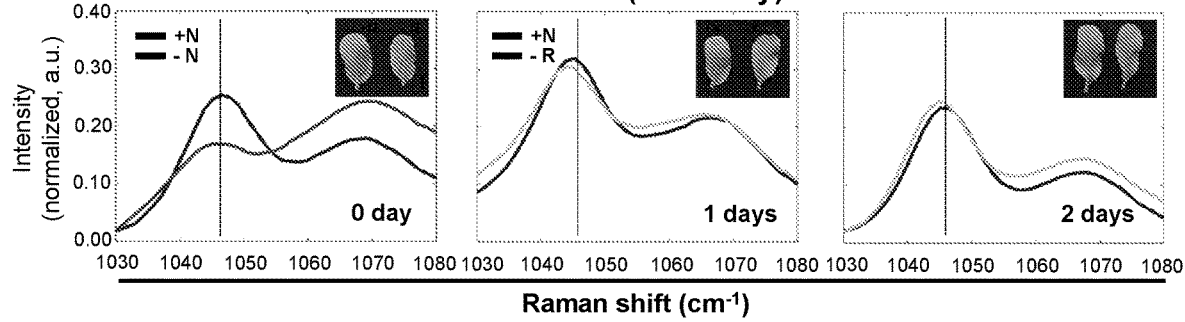
Figure 14:
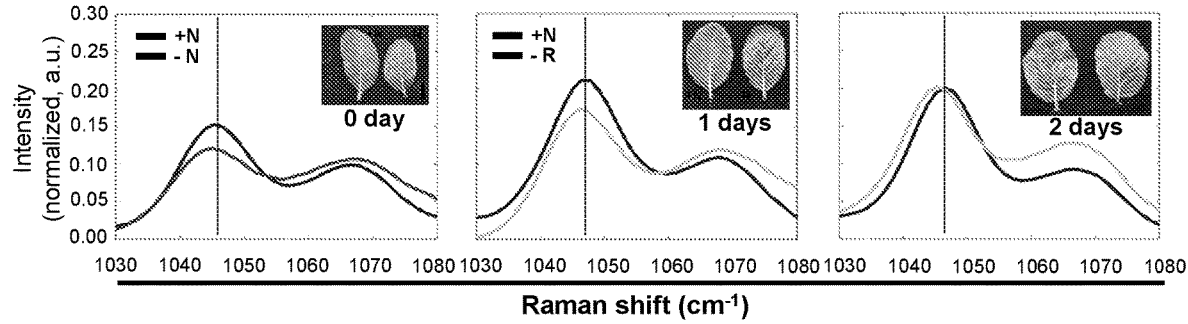
Figure 15:
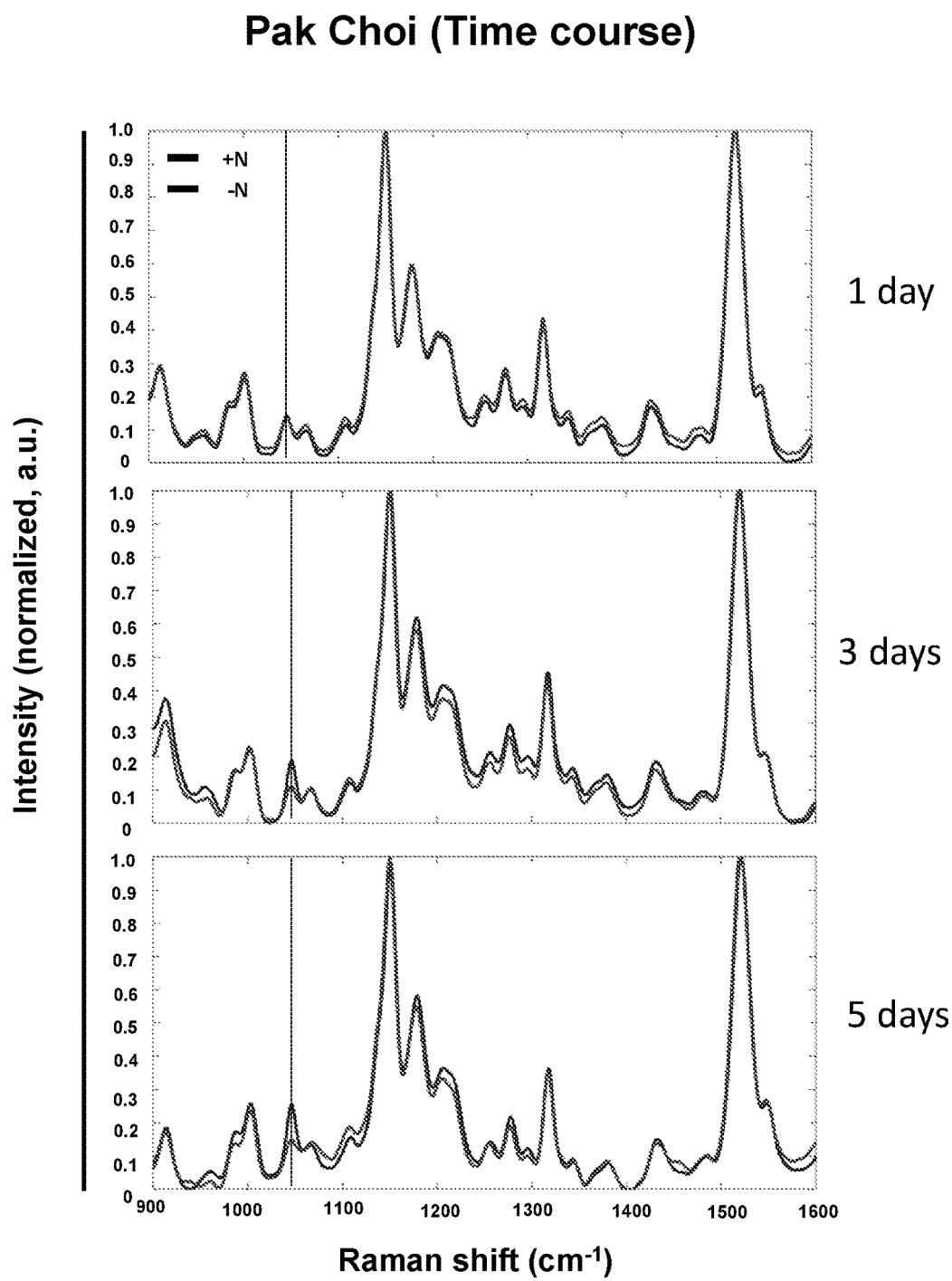
FIG. 15 shows Raman spectroscopic analysis of leafy vegetables, Pak Choi under +N or −N condition by time course. See FIG. 14A legend for details.
Figure 16:
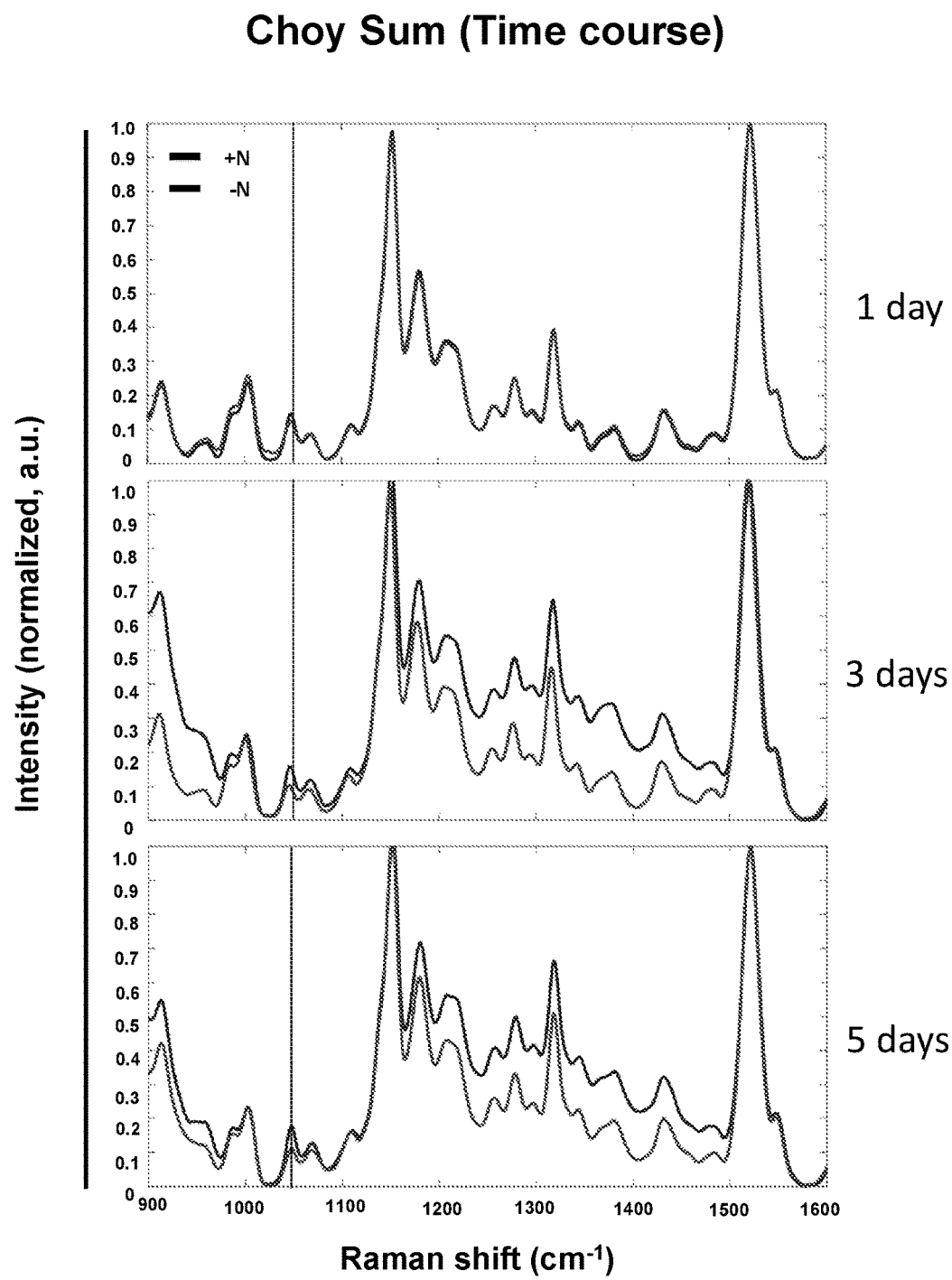
FIG. 16 shows Raman spectroscopic analysis of leafy vegetables, Choy Sum under +N or −N condition by time course. See FIG. 14B legend for details.
Figure 17:
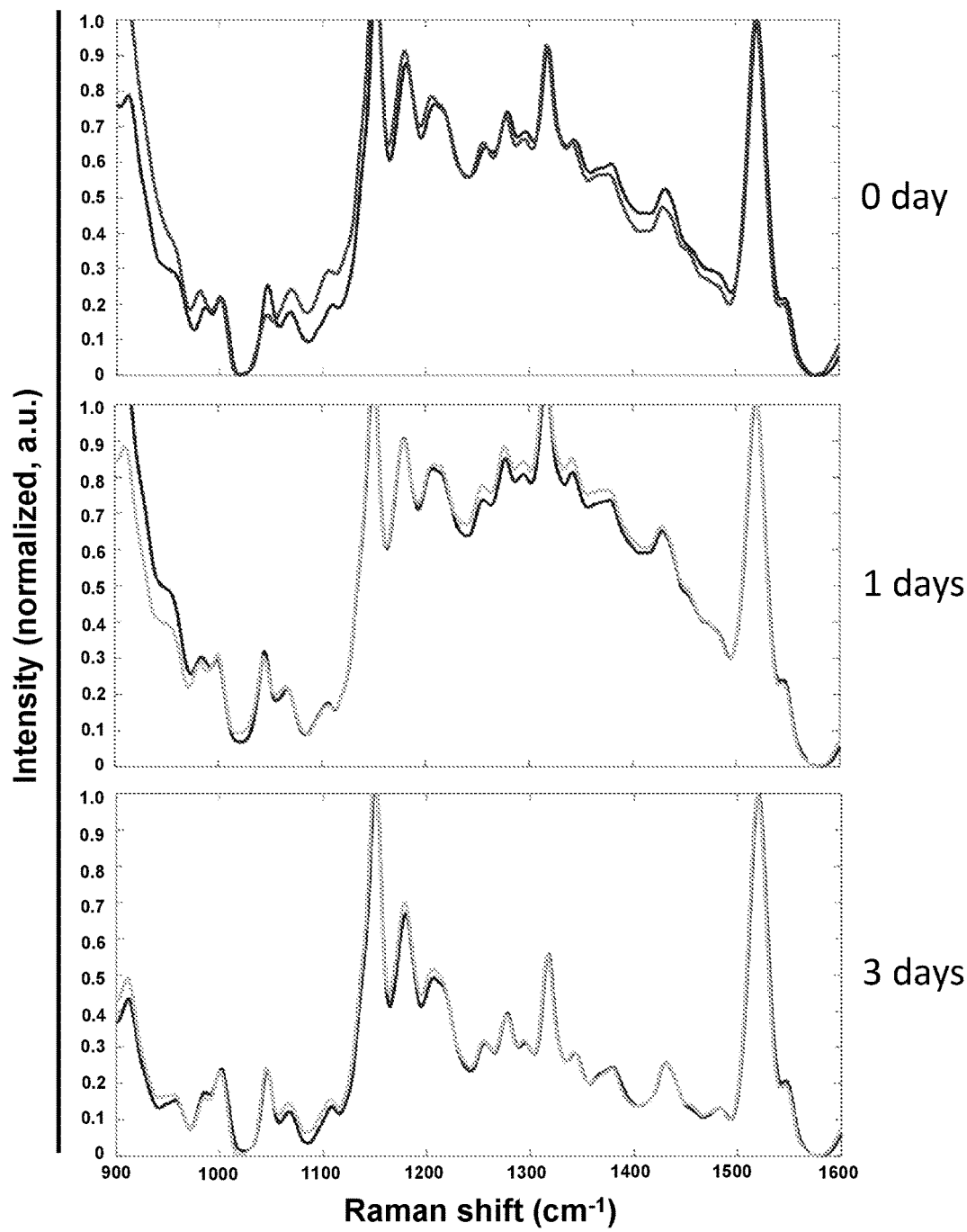
FIG. 17 shows a comparative analysis of wide-range Raman spectrum of leafy vegetables, Pak Choi grown for recovery experiments by time course. See FIG. 14C legend for details.
Figure 18:
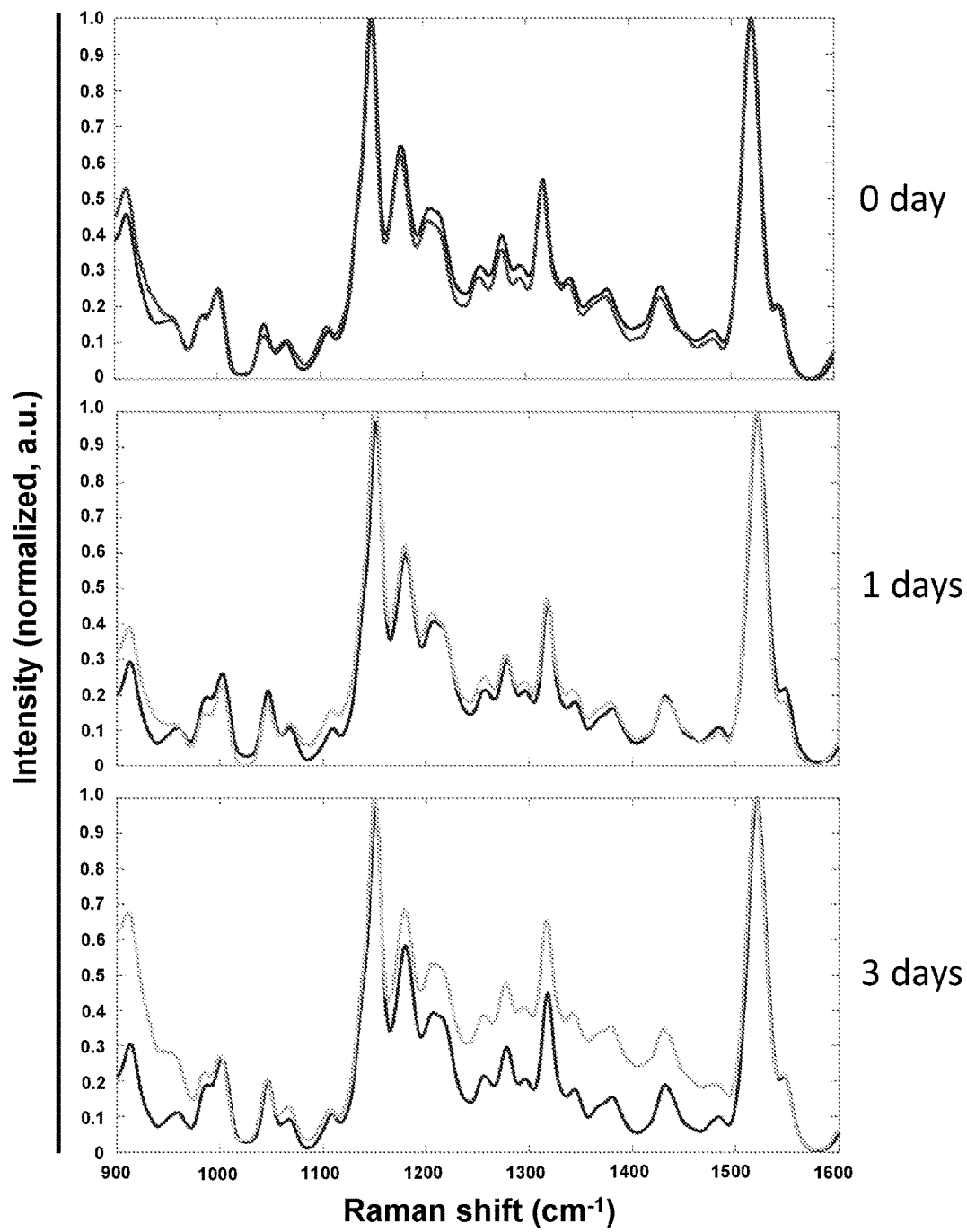
FIG. 18 shows a comparative analysis of wide-range Raman spectrum of leafy vegetables, Choy um grown for recovery experiments by time course. See FIG. 14D legend for details.

Similar experiments with the two leafy vegetable plants (Pak Choi and Choy Sum) showed that the intensity of the 1046 $cm^{-1}$ peak also decreased after 3 and 5 days in the −N medium compared with 1 day in the same medium (FIGS. 14A, 14B). To see if this decrease in peak intensity at 1046 $cm^{-1}$ can be reversed we transferred −N (day 3) plants to +N medium and followed their recovery for several days. FIGS. 14C and 14D show after one day in the +N recovery medium the nitrate peak intensity at 1046 $cm^{-1}$ was still lower than that of plants under continuous +N condition. However, the peak intensity returned to the level of that of +N plants after 3 days of recovery in the +N medium. FIGS. 15, 16, 17 and 18 show the corresponding wider-range spectra of FIGS. 14A, 14B, 14C and 14D, respectively.

Figure 19:
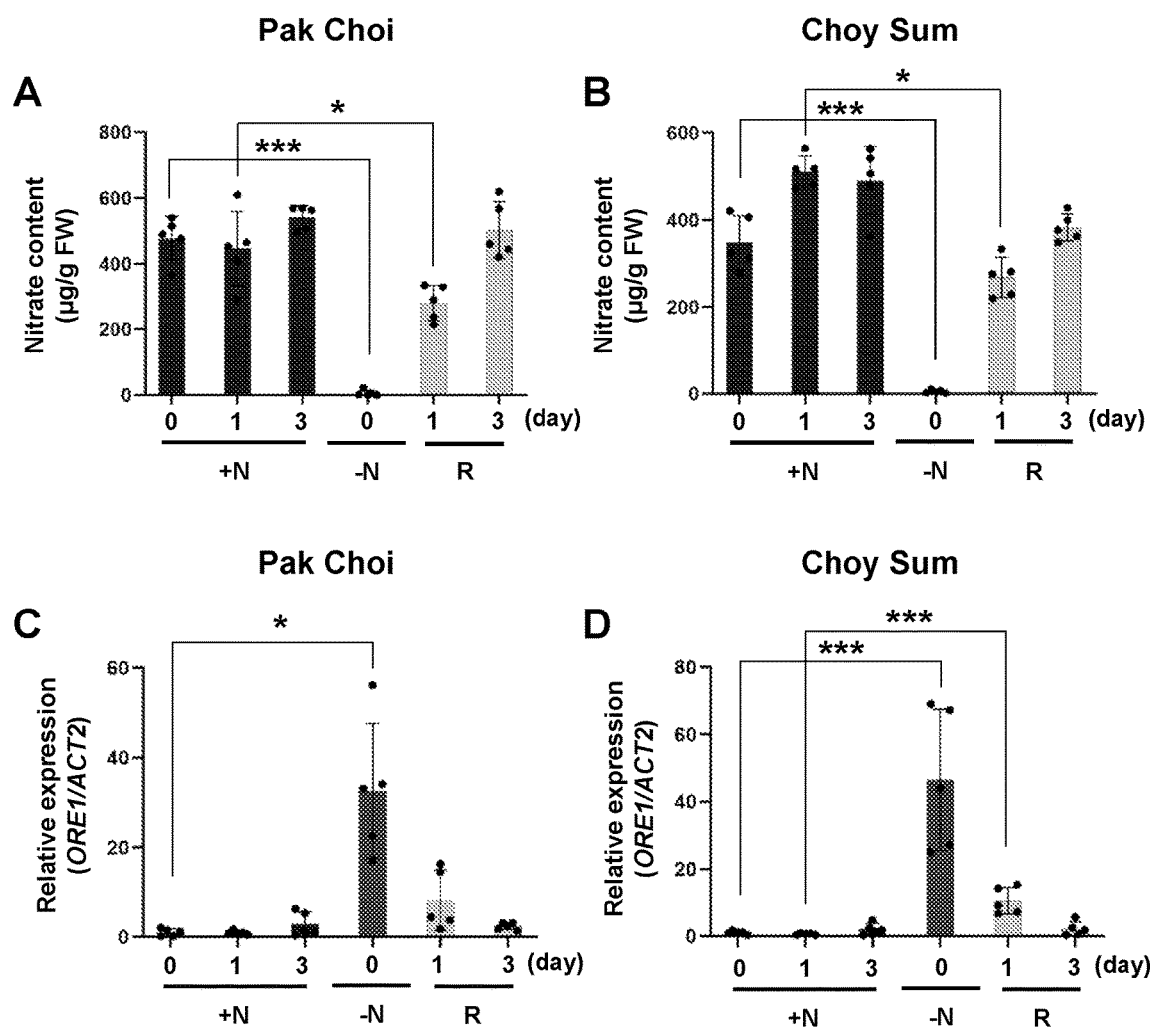
FIGS. 19A-19D show Nitrate content and ORE1 orthologous gene expression levels of two leafy vegetables in recovery experiments.

Nitrate content was measured and ORE1 orthologous gene transcript levels was analysed of the two leafy vegetable plants undergoing recovery in the full medium (FIG. 19). Compared with plants under continuous +N condition, the nitrate content of these −N Pak Choi and Choy Sum plants was decreased by 500-fold and 350-fold, respectively, but it returned to the +N level after 3 days in the +N medium. Changes in the nitrate content of the two leafy vegetables were paralleled by corresponding changes in the nitrate peak intensity (FIGS. 19A, 19B). Similar results were obtained with *Arabidopsis* ORE1 transcript levels (FIGS. 19C, 19D).

P-Value Data Tables

TABLE 2

P-value Data for FIGS. 4B/4C/4D and FIGS. 9B/9C/9D

| Plant | Chlorophyll content | Nitrate content | ORE1 transcript |
|---|---|---|---|
| *Arabidopsis* | 0.584535 | 2.61E−06 | 0.008142 |
| Pak Choi | 0.154849 | 4.37E−05 | 7.00406E−05 |
| Choy Sum | 0.385415 | 1.65E−06 | 0.000197 |

TABLE 3

P-value Data for FIG. 5D

| Plant | Nitrogen Deficiency | Phosphate Deficiency | Potassium deficiency |
|---|---|---|---|
| *Arabidopsis* | 0.005442373 | 0.406504012 | 0.875131679 |

TABLE 4

P-value Data for FIGS. 7B/7C/7D

| *Arabidopsis* (Col-0 and nrt2.1-2) | Chlorophyll content | Nitrate content | ORE1 transcript |
|---|---|---|---|
| +N medium | 0.873644 | 1.95271E−06 | 0.001194 |
| −N medium | 0.444163 | 0.000848 | 0.038968 |

TABLE 5

P-value Data for Intensity in FIGS. 7F and 9F

| Plants | Nitrate peak* |
|---|---|
| *Arabidopsis* (Col-0 and nrt2.1-2) (+N) | 8.30134E−06 |
| *Arabidopsis* (Col-0 and nrt2.1-2) (−N) | 0.008678788 |
| Pak Choi (−N) | 3.43089E−05 |
| Choy Sum (−N) | 0.001104344 |

*Nitrate peak indicated Raman spectrum at 1046 $cm^{-1}$ and normalized with carotenoids peak (1520 $cm^{-1}$). Table above lists P values of nutrient-deprived growth medium (−N, −P and −K, respectively) relative to Full medium as obtained from Student's t-test analysis (n = 14-16)

TABLE 6

P-value Data for FIGS. 11C and 11D

| *Arabidopsis* | Nitrate content | ORE1 transcript |
|---|---|---|
| +N and −N (0 d) | 1.4E−08 | 0.007870944 |
| +N and R (1 d) | 1.15E−11 | 0.028305343 |
| +N and R (2 d) | 7.71E−09 | 0.896780143 |
| +N and R (4 d) | 0.002985 | 0.118211177 |

TABLE 7

P-value Data for FIG. 19

| | Vegetables | Nitrate content | ORE1 transcript |
|---|---|---|---|
| Pak Choi | +N(0)and R(0) | 0.000761 | 0.0107838 |
| | +N(1)and R(1) | 0.037481 | 0.0641005 |
| | +N(3)and R(3) | 0.508053 | 0.7168413 |
| Choy Sum | +N(0)and R(0) | 0.000271 | 0.0085814 |
| | +N(1)and R(1) | 0.001392 | 0.0046007 |
| | +N(3)and R(3) | 0.071868 | 0.9882439 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Altangerel, N., Ariunbold, G. O., Gorman, C., Alkahtani, M. H., Borrego, E. J., Bohlmeyer, D., Hemmer, P., Kolomiets, M. V., Yuan, J. S., and Scully, M. O. (2017). In vivo diagnostics of early abiotic plant stress response via Raman spectroscopy. Proc Natl Acad Sci USA 114:3393-3396.

Baranski, R., Baranska, M., and Schulz, H. (2005). Changes in carotenoid content and distribution in living plant tissue can be observed and mapped in situ using NIR-FT-Raman spectroscopy. Planta 222:448-457.

C. M. Creely, G. P. Singh, and Petrov, D. (2005). Dual wavelength optical tweezers for confocal Raman spectroscopy. Optics Communications 245:465-470.

Carter, G. A. (1994). Ratios of leaf reflectances in narrow wavebands as indicators of plant stress. Int. J. Remote Sens. 15:697-703.

Charles Farber, and Kurouski, D. (2018). Detection and Identification of Plant Pathogens on Maize Kernels with a Hand-Held Raman Spectrometer. Analytical Chemistry 90:3009-3012.

D. A. Cataldo, M. Maroon, L. E. Schrader, and Youngs, V. L. (1975). Rapid colorimetric determination of nitrate in plant tissue by nitration of salicylic acid. Communications in Soil Science and Plant analysis 6:71-80.

D. E. Irish, and Walrafen, G. E. (1967). Raman and Infrared Spectral Studies of Aqueous Calcium Nitrate Solutions. J. Chem. Phys. 46:378.

Emmett W. Chappelle, Moon S. Kim, and III, J. E. M. (1992). Ratio Analysis of Reflectance Spectra (RARS): An Algorithm for the Remote Estimation of the Concentrations of Chlorophyll A, Chlorophyll B, and Carotenoids in Soybean Leaves Remote Sens. Environ. 39:239-247.

Gansel, X., Munos, S., Tillard, P., and Gojon, A. (2001). Differential regulation of the NO3− and NH4+ transporter genes AtNrt2.1 and AtAmt1.1 in *Arabidopsis*: relation with long-distance and local controls by N status of the plant. Plant J 26:143-155.

Grassmann, P. (1932). Der Ramaneffekt wässeriger Nitratlösungen. Zeitschrift für Physik 77:616-631.

Huang, Y. Y., Beal, C. M., Cai, W. W., Ruoff, R. S., and Terentjev, E. M. (2010). Micro-Raman spectroscopy of algae: composition analysis and fluorescence background behavior. Biotechnol Bioeng 105:889-898.

J. Peñuelas, J. A. Gamon, A. L. Fredeen, J. Merino, and C. B. Field. (1994). Reflectance Indices Associated with Physiological Changes in Nitrogen- and Water-Limited Sunflower Leaves. Remote Sens. Environ. 48:135-146.

Ju, X. T., Xing, G. X., Chen, X. P., Zhang, S. L., Zhang, L. J., Liu, X. J., Cui, Z. L., Yin, B., Christie, P., Zhu, Z. L., et al. (2009). Reducing environmental risk by improving N management in intensive Chinese agricultural systems. Proc. Natl. Acad. Sci. U.S.A. 106:3041-3046.

K. Ben Mabrouk, T. H. Kauffmann, and Fontana, M. D. (2013). Abilities of Raman sensor to probe pollutants in water. Journal of Physics: Conference Series 450: 012014.

Kant, S., Bi, Y. M., and Rothstein, S. J. (2011). Understanding plant response to nitrogen limitation for the improvement of crop nitrogen use efficiency. J. Exp. Bot. 62:1499-1509.

Lee Sanchez, Shankar Pant, Zhongliang Xing, Kranthi Mandadi, and Kurouski, D. (2019). Rapid and noninvasive diagnostics of Huanglongbing and nutrient deficits on citrus trees with a handheld Raman spectrometer. Analytical and Bioanalytical Chemistry 411:3125-3133.

Li, W., Wang, Y., Okamoto, M., Crawford, N. M., Siddiqi, M. Y., and Glass, A. D. (2007). Dissection of the AtNRT2.1:AtNRT2.2 inducible high-affinity nitrate transporter gene cluster. Plant Physiol 143:425-433.

Lieber, C. A., and A., M. J. (2003). Automated method for subtraction of fluorescence from biological Raman spectra. Appl. Spectrosc. 57:1363-1367.

Masclaux-Daubresse, C., Daniel-Vedele, F., Dechorgnat, J., Chardon, F., Gaufichon, L., and Suzuki, A. (2010). Nitrogen uptake, assimilation and remobilization in plants: challenges for sustainable and productive agriculture. Ann. Bot. 105:1141-1157.

Okamoto, M., Vidmar, J. J., and Glass, A. D. (2003). Regulation of NRT1 and NRT2 gene families of *Arabidopsis thaliana*: responses to nitrate provision. Plant Cell Physiol. 44:304-317.

Orsel, M., Krapp, A., and Daniel-Vedele, F. (2002). Analysis of the NRT2 nitrate transporter family in *Arabidopsis*. Structure and gene expression. Plant Physiol. 129:886-896.

Park, B. S., Yao, T., Seo, J. S., Wong, E. C. C., Mitsuda, N., Huang, C. H., and Chua, N. H. (2018). *Arabidopsis* NITROGEN LIMITATION ADAPTATION regulates ORE1 homeostasis during senescence induced by nitrogen deficiency. Nat. Plants 4:898-903.

Philip Heraud, B. R. W., John Beardall, and McNaughton, D. (2006). Effects of pre-processing of Raman spectra on in vivo classification of nutrient status of microalgal cells. J. Chemometrics 20: 193-197.

Pudney, P. D. A., Gambelli, L., and Gidley, M. (2011). Confocal Raman microspectroscopic study of the molecular status of carotenoids in tomato fruits and foods. Appl. Spectr. 65:127-134.

R. J. Porra, W. A. Thompson, and Kriedemann, P. E. (1989). Determination of accurate extinction coefficients and simultaneous equations for assaying chlorophylls a and b extracted with four different solvents: verification of the concentration of chlorophyll standards by atomic absorption spectroscopy. Biochimica et Biophysica Acta 975: 384-394.

Raman, C. V., and Krishnan, K. S. (1928). A New Type of Secondary Radiation. Nature 121:501-502.

Roberto Chirico, Salvatore Almaviva, Francesco Colao, Luca Fiorani, Marcello Nuvoli, Wenka Schweikert, Frank Schnürer, Luigi Cassioli, Silvana Grossi, Daniele Murra, et al. (2016). Proximal Detection of Traces of Energetic Materials with an Eye-Safe UV Raman Prototype Developed for Civil Applications. Sensors 16, 8; doi:10.3390/s16010008.

Santamaria, P. (2006). Nitrate in vegetables: toxicity, content, intake and EC regulation. J. Sci. Food Agric. 86:10-17.

Shi Ji-Yonga, Z. X. B., Zhao Jie-Wena, Wang Kai-Lianga, Chen Zheng-Wei, Huang Xiao-Wei, Zhang De-Tao, Mel Holmes. (2012). Nondestructive diagnostics of nitrogen deficiency by cucumber leaf chlorophyll distribution map based on near infrared hyperspectral imaging. Scientia Horticulturae 138:190-197.

Silveira, A., and Bauer, E. (1932). Compt. Rend. 195:416.

Tracy M. Blackmer, James S. Schepers, Gary E. Varvel, and Walter-Shea, E. A. (1996). Nitrogen Deficiency Detection Using Reflected Shortwave Radiation from Irrigated Corn Canopies. Agron. J. 88:1-5

What is claimed:

1. A method of diagnosing and reversing the development of nitrogen deficiency in a plant comprising:
   measuring nitrate in vivo and in situ in tissue of a plant leaf, using a Raman spectrometer, thereby;
   obtaining a Raman spectra, using near-infrared excitation wavelength, of nitrate in vivo and in situ in tissue of a plant leaf at a first point in time, wherein the Raman spectra includes a peak characteristic of nitrate;
   obtaining a Raman spectra, using near-infrared excitation wavelength, of nitrate in vivo and in situ in the tissue of the plant leaf at a second point in time, wherein the Raman spectra includes the peak characteristic of nitrate;
   comparing relative intensity of the peak characteristic of nitrate from the Raman spectra obtained at the first point of time with relative intensity of the peak characteristic of nitrate from the Raman spectra obtained at the second point of time;
   determining if there is a decrease in the relative intensity of the peak characteristic of nitrate from the Raman spectra obtained at the second point in time,
   wherein a relative decrease in intensity of the peak characteristic of nitrate from the Raman spectra obtained at the second point of time is indicative of nitrogen deficiency; and
   adding a source of nitrogen to the plant when nitrogen deficiency is indicated.

2. The method of claim 1, wherein the tissue of the plant leaf is a leaf blade.

3. The method of claim 1, wherein the peak characteristic of nitrate in the Raman spectra is 1046 $cm^{-1}$.

4. The method of claim 1, wherein the near-infrared excitation wavelength is 830 nm.

5. The method of claim 1, wherein obtaining the Raman spectra is non-invasive and non-destructive to the tissue of the plant leaf.

6. The method of claim 1, wherein nitrogen is added to the plant by fertilizing the plant.

7. A method of reversing development of nitrogen deficiency in a plant comprising:
   measuring nitrate in vivo and in situ in tissue of a plant leaf, using a Raman spectrometer, thereby;
   obtaining a Raman spectra, using near-infrared excitation wavelength, of nitrate in vivo and in situ in tissue of a plant leaf of the plant at a first point in time, wherein the Raman spectra includes a peak characteristic of nitrate;
   obtaining a Raman spectra, using near-infrared excitation wavelength, of nitrate in vivo and in situ in the tissue of the plant leaf at a second point in time, wherein the Raman spectra includes the peak characteristic of nitrate; and adding a source of nitrogen to the plant having nitrogen deficiency, wherein nitrogen deficiency is a relative decrease in intensity of the peak characteristic of nitrate from the Raman spectra at the second point in time compared to the intensity of the peak characteristic of nitrate from the Raman spectra at the first point in time.

8. The method of claim 7, wherein the tissue of the plant leaf is a leaf blade.

9. The method of claim 7, wherein obtaining the Raman spectra is non-invasive and non-destructive to the tissue of the plant leaf.

10. The method of claim 7, wherein nitrogen is added to the plant by fertilizing the plant.

11. The method of claim 7, wherein the peak characteristic of nitrate in the Raman spectra is 1046 $cm^{-1}$.

12. The method of claim 7, wherein the near-infrared excitation wavelength is 830 nm.

13. The method of claim 7, wherein the excitation wavelength is delivered using a laser power of about 100 mW or about 60 mW.

14. The method of claim 7, comprising obtaining the Raman spectra across an entire cross section of the plant leaf.

15. The method of claim 8, comprising obtaining the Raman spectra at two locations of the leaf blade.

16. The method of claim 15, wherein the two locations are on each side of a midvein of the leaf blade.

17. The method of claim 1, wherein the excitation wavelength is delivered using a laser power of about 100 mW or about 60 mW.

18. The method of claim 1, comprising obtaining the Raman spectra across an entire cross section of the plant leaf.

19. The method of claim 2, comprising obtaining the Raman spectra at two locations of the leaf blade.

20. The method of claim 19, wherein the two locations are on each side of a midvein of the leaf blade.

* * * * *

```
                           SEQUENCE LISTING

<160> NUMBER OF SEQ ID NOS: 19

<210> SEQ ID NO 1
<211> LENGTH: 24
<212> TYPE: DNA
<213> ORGANISM: Arabidopsis thaliana

<400> SEQUENCE: 1
cttaccatgg aaggctaaga tggg                                        24

<210> SEQ ID NO 2
<211> LENGTH: 22
<212> TYPE: DNA
<213> ORGANISM: Arabidopsis thaliana

<400> SEQUENCE: 2
tcgggtattt ccggtctctc ac                                          22

<210> SEQ ID NO 3
<211> LENGTH: 21
<212> TYPE: DNA
<213> ORGANISM: Brassica rapa

<400> SEQUENCE: 3
cgatgcatca agaatcggtg a                                           21

<210> SEQ ID NO 4
<211> LENGTH: 20
<212> TYPE: DNA
<213> ORGANISM: Brassica rapa

<400> SEQUENCE: 4
cggtggcaga gaagaaagtg                                             20

<210> SEQ ID NO 5
<211> LENGTH: 21
<212> TYPE: DNA
<213> ORGANISM: Brassica rapa

<400> SEQUENCE: 5
gggaagtcac ttgtgggtat g                                           21

<210> SEQ ID NO 6
<211> LENGTH: 20
<212> TYPE: DNA
<213> ORGANISM: Brassica rapa

<400> SEQUENCE: 6
ctttgtacca tcggcacgtt                                             20

<210> SEQ ID NO 7
<211> LENGTH: 20
<212> TYPE: DNA
<213> ORGANISM: Arabidopsis thaliana

<400> SEQUENCE: 7
tgagcaggag aagcagaaga                                             20
```

```
<210> SEQ ID NO 8
<211> LENGTH: 20
<212> TYPE: DNA
<213> ORGANISM: Arabidopsis thaliana

<400> SEQUENCE: 8
ttgttgggtg tgttctcagg                                              20

<210> SEQ ID NO 9
<211> LENGTH: 25
<212> TYPE: DNA
<213> ORGANISM: Arabidopsis thaliana

<400> SEQUENCE: 9
gctatgcttt ctcggtagat ggtag                                        25

<210> SEQ ID NO 10
<211> LENGTH: 25
<212> TYPE: DNA
<213> ORGANISM: Arabidopsis thaliana

<400> SEQUENCE: 10
aatgtcatgt ttggtgaggt taaga                                        25

<210> SEQ ID NO 11
<211> LENGTH: 23
<212> TYPE: DNA
<213> ORGANISM: Arabidopsis thaliana

<400> SEQUENCE: 11
agtggtcgta caaccggtat tgt                                          23

<210> SEQ ID NO 12
<211> LENGTH: 23
<212> TYPE: DNA
<213> ORGANISM: Arabidopsis thaliana

<400> SEQUENCE: 12
gatggcatga ggaagagaga aac                                          23

<210> SEQ ID NO 13
<211> LENGTH: 20
<212> TYPE: DNA
<213> ORGANISM: Brassica rapa

<400> SEQUENCE: 13
tgctggattc tggtgatggt                                              20

<210> SEQ ID NO 14
<211> LENGTH: 20
<212> TYPE: DNA
<213> ORGANISM: Brassica rapa

<400> SEQUENCE: 14
ggcgtgtgga agagagaaac                                              20

<210> SEQ ID NO 15
<211> LENGTH: 20
<212> TYPE: DNA
<213> ORGANISM: Brassica rapa

<400> SEQUENCE: 15
```

```
-continued tgctggattc tggtgatggt                                                    20

<210> SEQ ID NO 16
<211> LENGTH: 20
<212> TYPE: DNA
<213> ORGANISM: Brassica rapa

<400> SEQUENCE: 16
ggcgtgtgga agagagaaac                                                    20

<210> SEQ ID NO 17
<211> LENGTH: 19
<212> TYPE: DNA
<213> ORGANISM: Artificial Sequence
<220> FEATURE:
<223> OTHER INFORMATION: primer for genotyping

<400> SEQUENCE: 17
attttgccga tttcggaac                                                     19

<210> SEQ ID NO 18
<211> LENGTH: 21
<212> TYPE: DNA
<213> ORGANISM: Artificial Sequence
<220> FEATURE:
<223> OTHER INFORMATION: primer for genotyping

<400> SEQUENCE: 18
gttctccatg agcttcgtga g                                                  21

<210> SEQ ID NO 19
<211> LENGTH: 24
<212> TYPE: DNA
<213> ORGANISM: Artificial Sequence
<220> FEATURE:
<223> OTHER INFORMATION: primer for genotyping

<400> SEQUENCE: 19
cttaccatgg aaggctaaga tggg                                               24
```